US009314548B2

(12) United States Patent
Robeson et al.

(10) Patent No.: US 9,314,548 B2
(45) Date of Patent: *Apr. 19, 2016

(54) NANOSTRUCTURED SURFACES FOR BIOMEDICAL/BIOMATERIAL APPLICATIONS AND PROCESSES THEREOF

(71) Applicant: Liquidia Technologies, Inc., Morrisville, NC (US)

(72) Inventors: Lloyd Mahlon Robeson, Macungie, PA (US); Ginger Denison Rothrock, Durham, NC (US)

(73) Assignee: Liquidia Technologies, Inc., Morrisville, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/572,895

(22) Filed: Dec. 17, 2014

(65) Prior Publication Data

US 2015/0148903 A1 May 28, 2015

Related U.S. Application Data

(63) Continuation of application No. 12/087,374, filed as application No. PCT/US2007/000402 on Jan. 4, 2007, now Pat. No. 8,944,804.

(60) Provisional application No. 60/756,267, filed on Jan. 4, 2006.

(51) Int. Cl.
*A61L 27/16* (2006.01)
*H01L 29/06* (2006.01)
(Continued)

(52) U.S. Cl.
CPC .............. *A61L 27/16* (2013.01); *A61B 17/3417* (2013.01); *A61F 2/0077* (2013.01); *A61L 27/50* (2013.01);
(Continued)

(58) Field of Classification Search
CPC ....... A61L 27/16; A61L 27/50; A61L 31/048; A61L 31/14
USPC ................... 264/2.5, 219, 1.1, 293, 494, 496; 425/174.4, 385; 977/887, 840
See application file for complete search history.

(56) References Cited

U.S. PATENT DOCUMENTS

| 3,707,529 A | 12/1972 | Gladding et al. |
| 3,810,874 A | 5/1974 | Mitsch et al. |

(Continued)

FOREIGN PATENT DOCUMENTS

| EP | 0784064 B1 | 11/1999 |
| WO | 99/47570 A1 | 9/1999 |

(Continued)

OTHER PUBLICATIONS

Fissell et al. "Differentiated Growth of Human Renal Tubule Cells on Thin-Film and Nanostructured Materials." ASAIO Journal 2006, vol. 52, No. 3, pp. 221-227.

(Continued)

*Primary Examiner* — Joseph S Del Sole
*Assistant Examiner* — Nahida Sultana
(74) *Attorney, Agent, or Firm* — Morgan, Lewis & Bockius, LLP

(57) ABSTRACT

A medical device includes a textured surface having a predetermined nanostructure, wherein the nanostructure is less than about 500 nanometers in a broadest dimension. The textures nanostructure surface reduces friction between the medical device and biological tissue.

14 Claims, 9 Drawing Sheets

(51) Int. Cl.
*A61B 17/34* (2006.01)
*A61F 2/00* (2006.01)
*A61L 27/50* (2006.01)
*A61L 31/04* (2006.01)
*A61L 31/14* (2006.01)

(52) U.S. Cl.
CPC ............... *A61L 31/048* (2013.01); *A61L 31/14* (2013.01); *H01L 29/06* (2013.01); *A61F 2002/0081* (2013.01); *A61L 2400/12* (2013.01); *A61L 2400/18* (2013.01); *Y10S 977/84* (2013.01); *Y10S 977/887* (2013.01)

(56) References Cited

U.S. PATENT DOCUMENTS

| | | | |
|---|---|---|---|
| 3,810,875 | A | 5/1974 | Rice |
| 4,094,911 | A | 6/1978 | Mitsch et al. |
| 4,440,918 | A | 4/1984 | Rice et al. |
| 4,472,480 | A | 9/1984 | Olson |
| 4,694,045 | A | 9/1987 | Moore |
| 4,818,801 | A | 4/1989 | Rice et al. |
| 5,151,492 | A | 9/1992 | Abe et al. |
| 5,158,717 | A | 10/1992 | Lai |
| 5,674,959 | A | 10/1997 | Arcella et al. |
| 5,717,036 | A | 2/1998 | Saito et al. |
| 6,512,063 | B2 | 1/2003 | Tang |
| 6,669,785 | B2 | 12/2003 | DeYoung et al. |
| 6,884,847 | B2 | 4/2005 | Irie et al. |
| 8,128,393 | B2 | 3/2012 | Rolland et al. |
| 8,439,666 | B2 | 5/2013 | Rolland et al. |
| 8,545,865 | B2 | 10/2013 | Boden |
| 8,662,878 | B2 | 3/2014 | Rolland et al. |
| 2003/0228546 | A1 | 12/2003 | Nagahara et al. |
| 2004/0256764 | A1 | 12/2004 | Choi et al. |
| 2005/0142315 | A1 | 6/2005 | DeSimone et al. |
| 2005/0271794 | A1 | 12/2005 | DeSimone et al. |
| 2005/0273146 | A1 | 12/2005 | DeSimone et al. |
| 2006/0110125 | A1 | 5/2006 | Lin et al. |
| 2007/0175193 | A1 | 8/2007 | Niakan |
| 2007/0178133 | A1 | 8/2007 | Rolland |
| 2007/0254278 | A1 | 11/2007 | DeSimone et al. |
| 2007/0280983 | A1* | 12/2007 | Strickler et al. ............. 424/422 |
| 2008/0220041 | A1* | 9/2008 | Brito et al. .................. 424/423 |
| 2009/0028910 | A1 | 1/2009 | DeSimone et al. |
| 2009/0121370 | A1 | 5/2009 | Barrows et al. |
| 2009/0131959 | A1 | 5/2009 | Rolland |
| 2009/0250588 | A1 | 10/2009 | Robeson et al. |
| 2009/0281250 | A1 | 11/2009 | DeSimone et al. |
| 2010/0016514 | A1* | 1/2010 | Qiu ...................... B29D 11/00 525/327.4 |
| 2010/0196277 | A1 | 8/2010 | DeSimone et al. |
| 2011/0031651 | A1 | 2/2011 | Xu et al. |
| 2011/0257040 | A1 | 10/2011 | Turner et al. |
| 2011/0301716 | A1* | 12/2011 | Sirivisoot et al. .......... 623/23.53 |
| 2012/0132930 | A1 | 5/2012 | Young et al. |
| 2012/0156434 | A1 | 6/2012 | Satoh et al. |
| 2012/0183773 | A1* | 7/2012 | An et al. ...................... 428/402 |
| 2012/0275026 | A1 | 11/2012 | Zhou et al. |
| 2012/0276333 | A1* | 11/2012 | Hong ................... B29C 59/022 428/141 |
| 2013/0099211 | A1 | 4/2013 | Katz et al. |
| 2013/0127299 | A1 | 5/2013 | Kim et al. |
| 2013/0136818 | A1 | 5/2013 | Uehara et al. |
| 2013/0136998 | A1 | 5/2013 | Hwang et al. |
| 2013/0266761 | A1* | 10/2013 | Ho et al. ...................... 428/141 |
| 2013/0267455 | A1* | 10/2013 | Hauser et al. ................. 514/1.1 |
| 2013/0292879 | A1* | 11/2013 | Disawal et al. ............ 264/328.2 |
| 2014/0021450 | A1 | 1/2014 | Young et al. |
| 2015/0236620 | A1* | 8/2015 | Shao ...................... H02N 2/22 310/319 |
| 2015/0241908 | A1* | 8/2015 | Ozyilmaz ............. H01L 41/193 345/174 |

FOREIGN PATENT DOCUMENTS

| | | |
|---|---|---|
| WO | 02/094368 A1 | 11/2002 |
| WO | 2005/065324 A2 | 7/2005 |
| WO | 2005/084582 A1 | 9/2005 |
| WO | 2005/101466 | 10/2005 |
| WO | 2006/096793 A2 | 9/2006 |
| WO | 2006/116404 A2 | 11/2006 |
| WO | 2007/012114 A1 | 1/2007 |
| WO | 2007/021620 A2 | 2/2007 |
| WO | 2007/056561 A2 | 5/2007 |
| WO | 2007/081876 A3 | 7/2007 |

OTHER PUBLICATIONS

Mills et al. "Transparent micro- and nanopatterned poly(lactic acid) for biomedical applications." Journal of Biomedical Materials Research Part A 2006, vol. 76A, No. 4, pp. 781-787.

Barbucci et al. "Micro and nano-structured surfaces." Journal of Materials Science: Materials in Medicine 2003, vol. 14, pp. 721-725.

Haberstroh et al. "Polymers with Nanostructured Surface Features for Soft Tissue Replacement Applications." Materials Science Forum 2003, vols. 426-432, pp. 3115-3120.

Maynor et al. "Molding of Biologically-Derived Soft Nanostructures Using Pattern Replication in Non-wetting Templates (PRINT)." Polymeric Materials: Science & Engineering 2005, vol. 93, pp. 254-255.

Lim et al. "Polymer demixed nanotopographic surfaces provide nonbiological cell-stimulating cues." Polymer Preprints 2005, vol. 46, No. 2, p. 1277.

Lim et al. "Cell Sensing and Response to Micro- and Nanostructured Surfaces Produced by Chemical and Topographic Patterning." Tissue Engineering 2007, vol. 13, No. 8, pp. 1879-1891.

Miller et al. "PLGA nanometer surface features manipulate fibronectin interactions for improved vascular cell adhesion." Journal of Biomedical Materials Research Part A 2007, vol. 81A, pp. 678-684.

Clayton et al. "Perfluoropolyether Synthesis in Liquid Carbon Dioxide by Hexafluoropropylene Photooxidation." Macromolecules 1999, vol. 32, No. 24, pp. 8224-8226.

Choi et al. "A Photocurable Poly(dimethylsiloxane) Chemistry Designed for Soft Lithographic Molding and Printing in the Nanometer Range." JACS 2003, vol. 125, No. 14, pp. 4060-4061.

Rolland et al. "Solvent-Resistant Photocurable 'Liquid Teflon' for Microfluidic Device Fabrication." JACS 2004, vol. 126, No. 8, pp. 2322-2323.

Quake et al. "From Micro- to Nanofabrication with Soft Materials." Science Nov. 24, 2000, vol. 290, pp. 1536-1540.

Byck et al. "Polymeric Materials for Circulatory Assist Devices," Artificial Heart Program Conference Proceedings Jun. 9-13, 1969, pp. 123-132.

Turri et al. "End Group Chemistry of Fluoro-Oligomers: Highly Selective Syntheses of Diepoxy, Diallyl, and Tetraol Derivatives." Journal of Polymer Science, Part A: Polymer Chemistry 1996, vol. 34, pp. 3263-3275.

Priola et al. "UV-curable systems containing perfluoropolyether structures: synthesis and characterisation." Macromol. Chem. Phys. 1997, vol. 198, pp. 1893-1907.

Rolland et al. "Direct Fabrication and Harvesting of Monodisperse, Shape-Specific Nanobiomaterials." JACS 2005, vol. 127, No. 28, pp. 10096-10100.

Fu et al. "Reversible Control of Free Energy and Topography of Nanostructured Surfaces." JACS 2004, vol. 126, No. 29, pp. 8904-8905.

http://www.thefreedictionary.com/mould [Harper Collins Publishers 1995, 2002].

Rolland et al. "High Resolution Soft Lithography: Enabling Materials for Nanotechnologies." Angew, Chem. Jun. 29, 2004.

* cited by examiner

NANOSTRUCTURED SURFACES FOR BIOMEDICAL/BIOMATERIAL APPLICATIONS AND PROCESSES THEREOF

CROSS-REFERENCE TO RELATED APPLICATIONS

This application is a continuation of U.S. patent application Ser. No. 12/087,374, filed on Jan. 4, 2007, now U.S. Pat. No. 8,944,804, which is a U.S. National Stage of International Application No. PCT/US2007/000402, filed Jan. 4, 2007, which claims the benefit of U.S. Provisional Application No. 60/756,267, filed Jan. 4, 2006, all of which are incorporated herein by reference in their entireties.

TECHNICAL FIELD OF THE INVENTION

Generally, the present invention relates to biomedical/biomaterials with nanostructured surfaces and processes for producing or replicating the nanostructured surfaces. The nanostructured surfaces can be naturally occurring or synthetic structures and can impart increased utility for biomedical uses to the underlying article or substrate.

BACKGROUND OF THE INVENTION

The field of biomaterials has been an area of intensive research for decades. Biocompatibility of synthetic materials with biological tissue has been a major goal of developing synthetic materials to solve medical problems and facilitate the repair mechanisms of living organisms (specifically animal/human). Often synthetic materials are rejected by the in-vivo application of such materials. The complex aspects of compatibility of synthetic and biological systems are not well-recognized and the search for biocompatible systems has often centered on the chemical structure of synthetic materials. In the area of blood compatibility, for example, heparin-like surfaces have been intensively studied with synthetic polyelectrolyte complexes being an area of promising results but not effective enough for practical utility. Other studies have concluded that reduced surface free energy is desired and indeed surfaces such as silicone rubber and PTFE (e.g., Teflon® fluoropolymers), show improved blood compatibility over higher surface energy polymers but far from acceptable results. One approach has been to provide scaffolds for cell growth for coating synthetic polymers to provide compatibility (e.g. blood compatibility). One of the earliest references to this approach involved the utilization of a non-woven polypropylene microfiber web attached to a synthetic substrate (e.g. thermoplastic polyurethane) with Parylene C deposited by vacuum deposition/polymerization (Byck, J. S., Chow, S., Gonsior, L. J., Miller, W. A., Mulvaney, W. P., Robeson, L. M. and Spivack, M. A., in *Polymeric Materials for Circulatory Assist Devices; Artificial Heart Program Conference Proceedings*, Hegyeli, R. J. (Ed) (1969) U.S. Printing Office, Washington, D.C., p. 123). The microfiber web allowed for the endothelial cell adhesion and growth providing the blood compatibility to artificial heart surfaces. Although some success was achieved, this approach was not deemed practical due to severe material requirements and time/effort involved with cell growth. Other biomaterials such as wound coverings, stents, bone reconstruction, hip replacement, heart valves also require biocompatibility. Each system may require unique approaches towards achieving the desired biocompatibility. While the emphasis in biomaterials research has been placed on the chemical structure of the synthetic materials, the recognition that the surface morphology may play a key role is a recent development. A number of approaches have been proposed and experimental research has been reported showing promising trends/results relative to nano-structured surfaces. These approaches include phase separated blends and carbon nanotube surfaces.

A biomimetic/nanotechnology analysis has well-demonstrated the unique properties observed in nature for specific nanostructured surfaces. Synthetic approaches offering analogous surfaces have also demonstrated the unique surfaces. The synthetic approaches reported, however, are not viable/economic methods for achieving such systems for large scale utility. Methods/processes are needed to transform the biomimetic/nanotechnology observations into practical approaches for achieving obtaining biomedical materials. There is a need in this art for a method capable of replicating these features or surfaces at nano-scale dimensions that is scaleable to provide relatively large areas with these features. There is also a need in this art for a process that produces continuous nano-structured surfaces using a wide range of polymers. The instant invention discloses a methodology that can translate the biomimetic/nanotechnology concepts into viable/economic approaches to utilize the unique characteristics inspired by nature.

SUMMARY OF THE INVENTION

According to some embodiments of the present invention, a medical device includes a medical article having a textured surface with a predetermined nanostructure and where the nanostructure is less than about 500 nanometers in a broadest dimension. The predetermined nanostructure of the medical article is positioned on a biological tissue engaging surface of the medical article. The predetermined nanostructure comprises a plurality of repetitive nanostructures. The medical article includes a tissue penetrating device and the predetermined nanostructure is positioned on a skin engaging surface of the tissue penetrating device. The medical article includes a needle and the predetermined nanostructure is positioned on a skin engaging surface of the needle. The predetermined nanostructure is less than about 250 nanometers in a largest dimension. The predetermined nanostructure is less than about 100 nanometers in a largest dimension. The predetermined nanostructure is less than about 75 nanometers in a largest dimension. The predetermined nanostructure is less than about 50 nanometers in a largest dimension.

In other embodiments, a medical device includes a medical article having a biological tissue contacting portion, a polymer coating on a portion of the biological tissue contacting portion of the medical article, and a predetermined nanostructure on a portion of the polymer coating that communicates with the biological tissue wherein the predetermined nanostructure is less than 500 nanometers in a largest dimension.

According to other embodiments, a medical implant includes an artificial biological component, wherein the artificial biological component includes a textured tissue engaging surface, and wherein the textured tissue engaging surface includes a predetermined nanostructure having a maximum cross-sectional dimension less than about 500 nanometers in diameter.

According to yet another embodiment of the present invention, a method of medical treatment includes texturing a patient engaging portion of a medical article with a nanostructure, wherein the nanostructure includes three dimensional structures having a size less than about 500 nanometers in a broadest dimension and penetrating tissue with the textured medical article.

BRIEF DESCRIPTION OF THE DRAWINGS

FIG. 5A shows a segment of natural bovine heart chamber wall and FIG. 5B shows a PFPE replicate of the natural nanostructure of the segment of natural bovine heart chamber wall tissue;

DETAILED DESCRIPTION OF PREFERRED EMBODIMENTS

I. Non-Exhaustive Definitions

Figure 1:
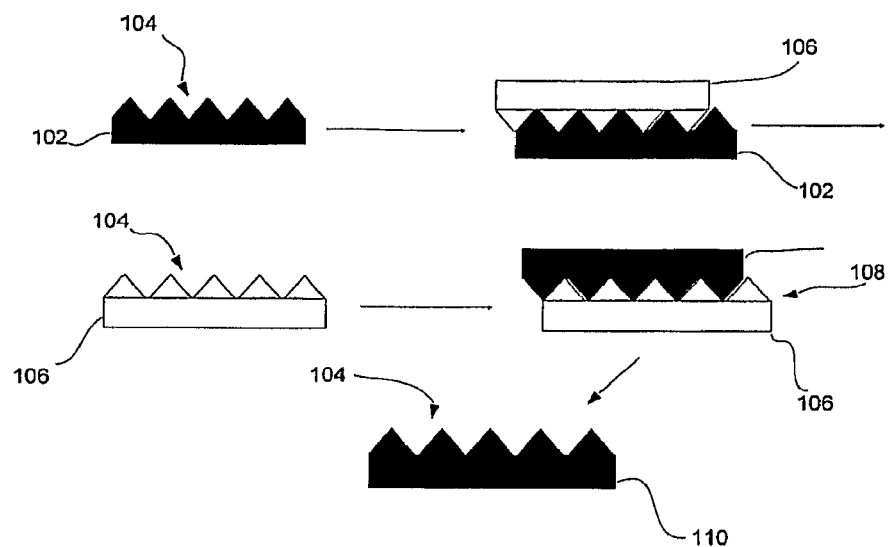
FIG. 1 is a schematic of a replicated nanostructure according to an embodiment of the present invention.

The following definitions are used in describing certain aspects of the instant invention:

Master template: The master template is the original surface desired to be replicated or reproduced. This surface can be a naturally occurring plant or animal surface or mineral or a synthetically produced nanostructured surface.

Templating polymer: The templating polymer is the polymer produced from a liquid monomer, oligomer or prepolymer precursor polymerized on the master template surface and released. This "negative" is employed for producing the desired product with a surface morphology substantially equal to the master template.

Templated polymer: The templated polymer is the polymer produced from a liquid monomer, oligomer or prepolymer precursor by polymerization on the templating polymer surface. The templated polymer becomes the positive replication of the master template.

As used herein, the term "nanostructure" can mean an array, a matrix, specific shape or form, a template of an article of interest, a two-dimensional shape, a three-dimensional shape, or the like. In some embodiments, a nanostructure can be a single nanostructure, multiple nanostructures, ordered nanostructures, uniform nanostructures, repetitious nanostructures, alternating nanostructures, regular nanostructures, irregular nanostructures, or random arrays or templates of nanostructures. The nanostructures of the present invention can also include micro- and/or nano-sized cavities or micro- or nano-sized projections.

As used herein, the term "partial cure" refers to a condition where only a portion of a polymerizable group of a material is reacted. In certain embodiments, the term "partially-cured material" refers to a material that has undergone a partial cure process or treatment.

As used herein, the term "full cure" refers to a condition wherein a majority of a the polymerizable group of a material is reacted. In certain embodiments, the term "fully-cured material" refers to a material which has undergone a full cure process or treatment.

As used herein, the term "photocured" refers to a reaction of polymerizable groups whereby the reaction can be triggered by actinic radiation, such as UV light. In this application UV-cured can be a synonym for photocured.

As used herein, the term "thermal cure" or "thermally cured" refers to a reaction of polymerizable groups, whereby the reaction can be triggered or accelerated by heating the material beyond a threshold temperature.

II. Introduction

The instant invention relates broadly to nanostructured surfaces for biomedical/biomaterials applications and processes for producing such nanostructured surfaces. According to an embodiment, medical probe type devices are coated with materials and materials having nanostructured surfaces for reducing friction, adhesion, absorption, adsorption, contamination, and the like. Examples of such medical probe type devices includes, but are not limited to, catheters, surgical probes, stent insertion probes, surgical needles, and the like. According to another embodiment, the present invention includes templating a natural surface, such as a surface of a human system (e.g., heart valves, interior of blood vessels, skin, lung tissue, liver tissue, kidney tissue, nerves, and the like) to replicate a natural surface nanostructure.

III. Description

According to some embodiments as shown in FIG. 1, nanostructured surfaces of medical articles are fabricated by providing a templating polymer mold having a nanostructured surface "negative" spaced adjacent to or surrounding the medical article. Monomers, oligomers or prepolymers are then placed between the medical article and the templating polymer mold and polymerized. The resultant article thereby acquires the nanostructured surface of the templating polymer mold and has the desired predetermined nanostructured surface. In some embodiments, to prepare the templating polymer mold, a master article or master template 102, (FIG. 1) such as a synthetic surface (e.g., medical device, needle, catheter, probe, stent, and the like) is prepared with the desired nanostructured surface 104. The nanostructured surface can be prepared on the synthetic surface by lithographic techniques, by etching, chemical vapor deposition, selective extraction of phase separated polymer blends, selective removal of block copolymer structures (e.g., selective degradation of one constituent), anodized alumina, carbon nanotube arrays, among other processes. The liquid monomer, oligomer or prepolymer of the templating polymer 106 is then contacted with the master template 102 and polymerized. The resultant polymer can then be employed as the mold 108 for duplicating the nanostructured surface 104, as described supra, to form templated replica 110.

Figure 2:
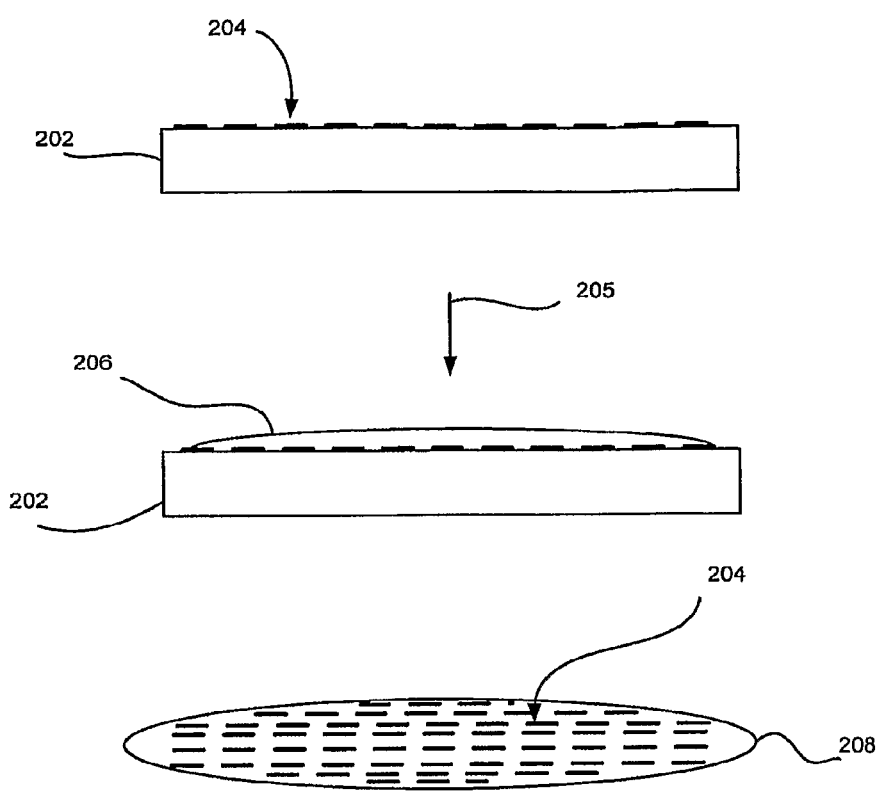
FIG. 2 is a schematic of a replicated nanostructured surface of a natural article according to an embodiment of the present invention.

According to another embodiment as shown in FIG. 2, master template includes a natural article 202 (e.g., biological tissue, artery, vein, muscle tissue, lung tissue, other human or animal tissues, bacteria, yeast, or the like). The natural article includes a surface with surface structures 204. The templating monomer, oligomer, or prepolymer liquid precursor 206 is contacted with the natural article 202 and polymerized to yield a "negative" pattern 208 of the natural article. This pattern 208 is then used as a template to reproduce the surface structure 204. For example, the interior of blood vessels can be reproduced and used to coat stents. As the surface nanostructure is believed to be an important aspect of compatibility of synthetic materials with specific biological systems, replication of the biological surface on the nanoscale is an important aspect for achieving enhanced biocompatibility.

The nanostructure of the instant invention is related to reproducing or replicating a single or individual nano-structure (i.e., master template having biomedical utility) a plurality of times and across a relatively large surface (e.g., repeatedly replicating a nano-structured surface across a substrate thereby producing an article, a film, or coating having the nano-structure extending across a predetermined surface area). The instant invention also relates to reproducing or replicating the nano-structure as a continuous surface without repeatedly contacting the substrate with the master template (e.g., forming a mold, continuous belt or other tool including a templated polymer and using the templated polymer to form the nanostructure surface upon the substrate). In some embodiments nanostructured surface of the present invention can be fabricated according to methods, materials, and devices disclosed in U.S. patent application Ser. No. 11/633,763 filed Dec. 4, 2006, PCT International patent applications PCT/US06/23722 filed Jun. 19, 2006; PCT/US06/31067 filed Aug. 9, 2006; and PCT/US06/43756 filed Nov. 9, 2006; and U.S. Provisional Patent application 60/734,880 filed Nov. 9, 2005, each of which is incorporated herein by reference in its entirety. The nanostructured surface can impart improved biomedical utility to at least a portion of the substrate.

According to some embodiments of the present invention, the nanostructure to be replicated and that is replicated has an overall largest dimension of less than about 1000 nanometers. The overall largest dimension can be a cross-sectional dimension, a height protruding from a surface, a cavity depth, or the like. In alternative embodiments, the largest dimension of the nanostructure is less than about 750 nanometers. In alternative embodiments, the largest dimension of the nanostructure is less than about 500 nanometers. In alternative embodiments, the largest dimension of the nanostructure is less than about 400 nanometers. In alternative embodiments, the largest dimension of the nanostructure is less than about 300 nanometers. In alternative embodiments, the largest dimension of the nanostructure is less than about 250 nanometers. In alternative embodiments, the largest dimension of the nanostructure is less than about 200 nanometers. In alternative embodiments, the largest dimension of the nanostructure is less than about 150 nanometers. In alternative embodiments, the largest dimension of the nanostructure is less than about 100 nanometers. In alternative embodiments, the largest dimension of the nanostructure is less than about 90 nanometers. In alternative embodiments, the largest dimension of the nanostructure is less than about 80 nanometers. In alternative embodiments, the largest dimension of the nanostructure is less than about 70 nanometers. In alternative embodiments, the largest dimension of the nanostructure is less than about 60 nanometers. In alternative embodiments, the largest dimension of the nanostructure is less than about 50 nanometers. In alternative embodiments, the largest dimension of the nanostructure is less than about 40 nanometers. In alternative embodiments, the largest dimension of the nanostructure is less than about 30 nanometers. In alternative embodiments, the largest dimension of the nanostructure is less than about 20 nanometers. In alternative embodiments, the largest dimension of the nanostructure is less than about 10 nanometers. In alternative embodiments, the largest dimension of the nanostructure is less than about 5 nanometers.

In one aspect of the present invention, imprint lithography, initially developed for electronic applications, can be employed for producing the templated polymer that corresponds to the nano-structured surfaces. To produce, the nano-structured surfaces of this invention, low modulus, low surface energy and organic solvent/monomer resistant imprinting (templating) materials can be employed for producing continuous films of various materials. The templating material is polymerized from a liquid monomer or oligomer on a surface to be replicated (master template) by exposing the liquid to conditions whereby polymerization occurs. The master template can be a biological system (e.g. gecko foot), or a synthetic nanostructured surfaces. Examples of suitable synthetic surfaces include carbon nanotube "forests", lithographic methods designed to yield the desired structure (e.g. pillar arrays), crystal growth yielding needle like protrusions from the surface, selective extraction of phase separated polymer blends, sol-gel processes such as described in reference (J. T. Han et al., J. Am. Chem. Soc., 126, 4796 (2004)), and anodized aluminum oxide surfaces as described in reference (Q. Fu et al., J. Am. Chem. Soc., 126, 8904 (2004)), each of which is incorporated herein by reference in its entirety.

In another aspect of the present invention, the liquid templating system can be applied onto a nanostructured surface and polymerized while in contact with the nanostructured surface. Next, the polymerized material is released from the master template. Another polymer can then be polymerized on this polymer template to reproduce the structure of the master template such that the master template is reproduced numerous times. A schematic diagram of this process is illustrated FIG. 1. This can be repeated many times to develop an array of master templates and in turn an array of the templated surfaces, thereby assembling the replicated areas into a large area with surface morphology similar or substantially identical to the initial master template. This large area can be coated with the liquid prepolymer or liquid monomer to provide a high surface area for reproducing the nanostructured surface in a continuous process yielding a coating or film with one surface replicating the master template. The polymerized liquid prepolymer or liquid monomer can be employed as a belt to provide for a roll-to-roll or high throughput process. This nanostructured polymer belt can have monomer or liquid prepolymer added at one end of the belt followed by polymerization and then removed at the other end as a continuous nanostructured surface with surface morphology equivalent to the original master template. The thickness of the resultant film can be controlled by doctor blade, rollers, a predetermined applied pressure, by monitoring the addition amount of liquid prepolymer, combinations thereof, or the like. The liquid monomer or prepolymer can be polymerized by UV or peroxide initiated free radical polymerization, rapid condensation polymerization, ring opening polymerization, thermal curing, combinations thereof, other curing systems, and the like. If desired, sol-gel chemistry can also be employed to yield inorganic surfaces. The inorganic surfaces would generally need a substrate layer applied to the inorganic surface to allow for adequate toughness for flexible film utility. Modest pressure (from rollers or solid surfaces) may be desired to assure that the monomer or liquid prepolymer fills the nanostructured features of the template. Vacuum may also be required such that trapped air (or inert atmosphere) does not prevent flow of the prepolymer into the crevices of the template.

According to some embodiments, the prepolymer materials can be applied directly to living tissue to be replicated. According to such embodiments, the curing process is selected as a process that does not permanently damage the living tissue.

The nanostructured surfaces of the present invention can be employed in a wide array of biomedical/biomaterial applications. The nanostructured surfaces can be applied to various medical articles including, without limitation, surgical needles, surgical probes, catheters, drains, tubes, cannulas, and the like to reduce friction and resultant pain and tissue damage during their application. In some embodiments, the nanostructured surfaces are employed in blood contact applications to reduce and/or prevent blood coagulation in the presence of a foreign object. In other embodiments, the nanostructured surfaces are employed on the interior of arteries and veins, heart valves, artificial heart surfaces, stent surfaces, intra-aortic balloons, vascular graphs, blood transfusion systems, surgical bypass systems, combinations thereof, and the like. In some embodiments, the nanostructured surfaces are applicable to wound coverings, and artificial skin (e.g., bio-absorable materials).

According to some embodiments, the nanostructured surfaces of this invention can be applied to various medical implants including metallic, ceramic, and polymeric based systems including composite structures. The nanostructured surface features can be designed to increase biocompatibility using synthetically derived master templates or naturally/biologically occurring templates such as specific surfaces of the human anatomy (e.g., organs, tissues, cell surface structures, other naturally occurring surfaces, and the like). Medical implants utilizing nanostructured surfaces of the present invention can include, without limitation, heart valves, joint prosthesis components, hip and knee replacements, bone replacement, pacemaker coatings, cardiovertor/defibrillator device coatings, stents, vascular grafts, cochlear prosthesis, in-vivo diagnostic equipment, ocular devices, combinations thereof, and the like.

In another aspect of the invention, nano-structured surfaces yield improved properties for biomedical equipment by reducing friction. Surgical needles, stent insertion devices, catheters, and various medical related instruments involved with probing human tissue can benefit from reduced friction. In some embodiments, the probes can be coated with nanostructured surfaces fabricated from a low surface energy polymeric material, such as a fluorinated polymer including but not limited to fluoropolyether, perfluoropolyether, and the like, to yield reduced friction between the medical device and body tissue.

In some embodiments, the nanostructured surfaces of the present invention can be employed for articles employed in surgery including, without limitation, surgical drapes, coverings, wipes, and the like by using surfaces that are superhydrophobic, self-cleaning and/or resistant to bacterial attachment and biological staining. These coatings can also be used in bandaids/bandages to protect open wounds by having a superhydrophobic/non-stick surface which resists attachment/growth of unwanted biological species and allow for removal once the wound area begins healing or is healed.

In one aspect of the present invention, biological tissue can be templated to provide a scaffold that promotes tissue growth. In some embodiments, the biological tissue that is templated includes heart tissue, nerve tissue, vascular tissue, lung tissue, kidney tissue, liver tissue, stomach tissue, intestine tissue, ocular tissue, and the like. For example, in embodiments in which nerve tissue is templated to provide a scaffold that promotes nerve tissue growth, the nerve fibers/fibrils can be templated using actual nerves or analogous structures designed to promote desired growth. In other aspects of the present invention, the nanostructures of the present invention can be employed to provide scaffolds for organ functions (e.g. liver, kidney, intestines, heart, vascular, stomach, lung, and the like naturally occurring surfaces). These scaffolds can be templated from the organ surface or analogous synthetic structures. In alternative embodiments, cells can be embedded in the scaffold to promote cell growth and/or organ replication. In alternative embodiments, the cells used in the scaffolds and templating of the present invention can be patient indigenous cells, cells from a tissue culture, donor cells, patient indigenous stem cells, donor stem cells, combinations thereof, and the like.

The nanostructured films and coatings made by the inventive process can be useful for a myriad of applications. In some embodiments, the invention disclosure relates to a process by which continuous films or substrates can be produced which have nanostructured surfaces to yield improved biomedical properties to at least a portion of a broad range of films or substrates.

Some applications may not be capable of utilizing these films as the surface contours may not accommodate film coatings. A contoured substrate can have the desired nanostructured surface applied by a mold process involving a similar protocol. A master template offering the nanostructured surface can be covered with the templating polymer to produce the desired negative, such as the process shown in FIG. 2. A contoured surface can then be coated (adhered) with the templating polymer either directly or by transfer to the surface. This contoured surface would be designed to match the article contour such that both surfaces are in close proximity. A monomer, oligomer or prepolymer liquid can be placed between the two surfaces. After polymerization, the contoured surface coated with the templating polymer negative is removed from the article with the templated polymer polymerized between the surfaces staying on the article contour. The resultant article will thus have a nanostructured surface equal to the master template. As a subset of this aspect a flexible stamp including the templating polymer with a "negative" nanostructed surface of the master template can be conformally applied to a contoured surface with a layer of monomer, oligomer or prepolymer between the stamp and the contoured surface. Upon polymerization and release of the stamp, the contoured surface will have a nanostructured surface equal to the master template.

The nanostructured coatings and films can be applied to flat, curved, irregular, uniform, non-uniform, and the like surfaces and adhered with appropriate adhesives. In some applications, the interior of conduits can be coated by folding the nanostructured coatings into a tubular shape and adhering to the conduit interior surface.

In alternative embodiments, the replicated nanostructured surfaces can be fabricated into a medical article. In some embodiments, the medical article can include a thin layer of a first polymer material, such as for example, perfluoropolyether that includes the replicated nanostructure surface. If desired, and depending on the application, the thin polymer layer that includes the nanostructured surface can be adhered or associated with a second polymer, such as for example PDMS, which can act as the bulk material of the medical article.

The templating polymer employed as a continuous surface for roll-to-roll processing or as a stamp or mold system can be anchored unto a more rigid surface (substrate) using adhesives designed to maximize the interfacial adhesion between the templating polymer and the substrate. The substrate can be a metal (e.g. steel (or steel alloy), copper, aluminum) or a polymeric substrate such as polyethylene terephthalate) film. This would allow for more dimensional stability during the process of forming the templated polymer film or coating and can also be employed to prevent stamp collapse as noted by Huang et al. (Langmuir, 21, 8058 (2005)) to be a potential problem in soft lithography.

In certain aspects of this invention, nano-structured surfaces are discussed in detail. While many of the benefits of the templating approach noted herein are most effective at the nano scale of dimensions, conditions can also exist where microscale dimensions are also effective. The processes described herein are also contemplated for similar approaches to achieve microscale surface dimensions.

Figure 3A:
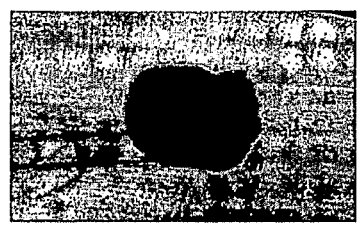
FIGS. 3A-3C show a replicated subclavian artery according to embodiments of the present invention.
Figure 3B:
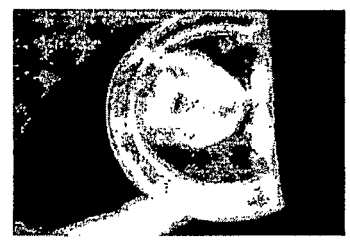
Figure 3C:
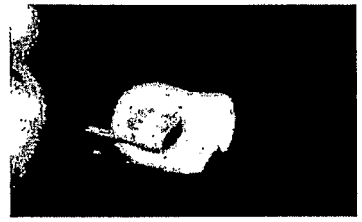

Referring now to FIG. 3A, an aorta and branches were surgically removed from a cow's heart and a 1-2" length section having 1" diameter of a subclavian artery was cut on cross-section and cleaned with DI water. A casting resin of polydimethylsiloxane (PDMS) was prepared and uncured PDMS was poured into a plastic container where the artery section was suspended, completely covering the artery. The PDMS was then cured at 75 OC for 30 minutes. The plastic container was removed from the oven, allowed to cool, and the plastic removed from the cured PDMS. The casting resin was sliced such that the end of the artery was exposed, and the artery was removed with tweezers leaving a PDMS mold of the artery, as shown in FIG. 3B. A PFPE replicate was from the PDMS mold leaving a cast replicate of the original artery, as shown in FIG. 3C.

Figure 4:
FIG. 4 shows sections of coronary arteries with PFPE plugs according to embodiments of the present invention.

Referring now to FIG. 4, the interior of coronary arteries were molded according to the present invention. 1 inch long sections of coronary arteries with surrounding tissue were dissected from a cow's heart. The end of the artery was sealed and PFPE-dimethacrylate (PFPE-DMA) containing 2,2-diethoxyacetophenone was injected into the open end of the artery. The two artery sections were placed in a curing chamber and cured. The sections were removed from the chamber and photographed, as shown in FIG. 4.

Figure 5A:
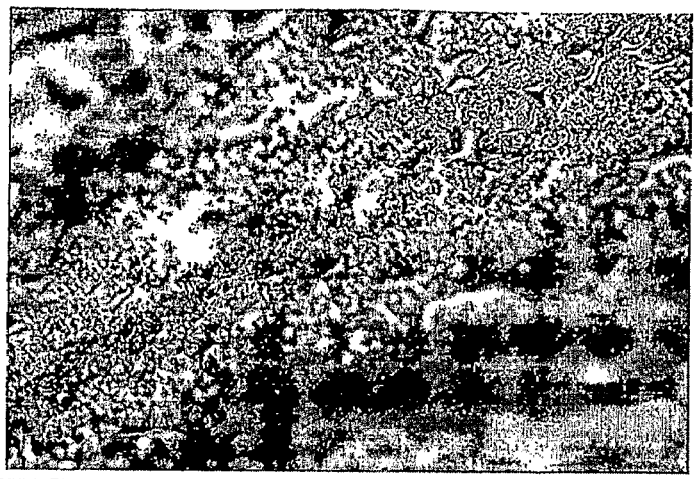
FIGS. 5A and 5B show replication of bovine heart muscle where
Figure 5B:

Referring next to FIG. 5, a PFPE replicate of heart muscle surface was fabricated according to methods and materials of the present invention. A 1.5"×1.5" section of a chamber of the heart was cut from a cow's heart, rinsed with DI water, and dried with compressed air and is shown in FIG. 5. PFPE-dimethacrylate (PFPE-DMA) containing 2,2-diethoxyacetophenone was coated onto the chamber wall surface and placed in a curing chamber. After the material was cured, the cured PFPE can be carefully peeled from the surface. Surface structure of the heart muscle was replicated onto the PFPE as shown in FIG. 5

Figure 6:
FIG. 6 shows replication of vessels within a porcine liver.

According to FIG. 6, a blood vessels in a liver was replicated according to methods and materials of the present invention. As shown in FIG. 6, a pig's liver was sectioned into 1 inch slices containing cross sections of blood vessels raging in diameter from 0.5 to 2 cm. One end of the vessels can be sealed and PFPE-dimethacrylate (PFPE-DMA) containing 2,2-diethoxyacetophenone injected into the vessels. The sections can then be placed in a curing chamber and cured. After the sections are removed from curing, surface structures can be seen, as shown in FIG. 6.

Figure 7:
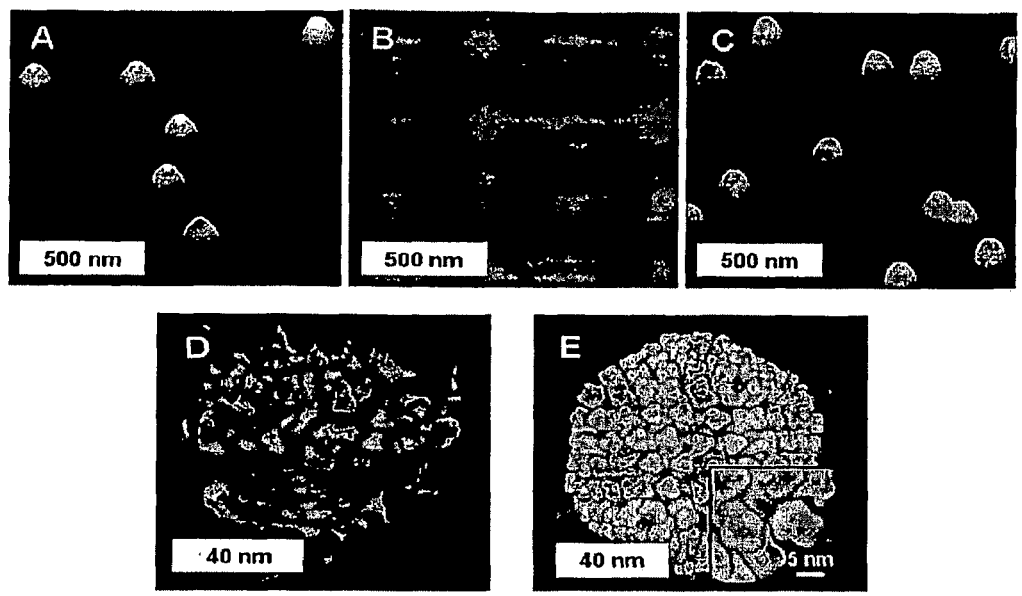
FIG. 7 shows AFM and TEMT images of molded and replicated adenovirus particles according to an embodiment of the present invention.

As shown in FIG. 7, an AFM and TEMT images depicts molding and replication of adenovirus particles. FIG. 7A shows an AFM image of an adenovirus master, prepared by depositing adenovirus particles onto a silicon surface. FIG. 7B shows an AFM image of a PFPE mold formed from an adenovirus master. FIG. 7C shows an AFM image of a triacrylate/bisphenol A dimethacryate adenovirus replica. FIG. 7D shows a TEMT reconstruction of a triacrylate/bisphenol A dimethacrylate adenovirus replica. Also, FIG. 7E shows a cryo-electron microscopy reconstruction of adenovirus.

Figure 8:
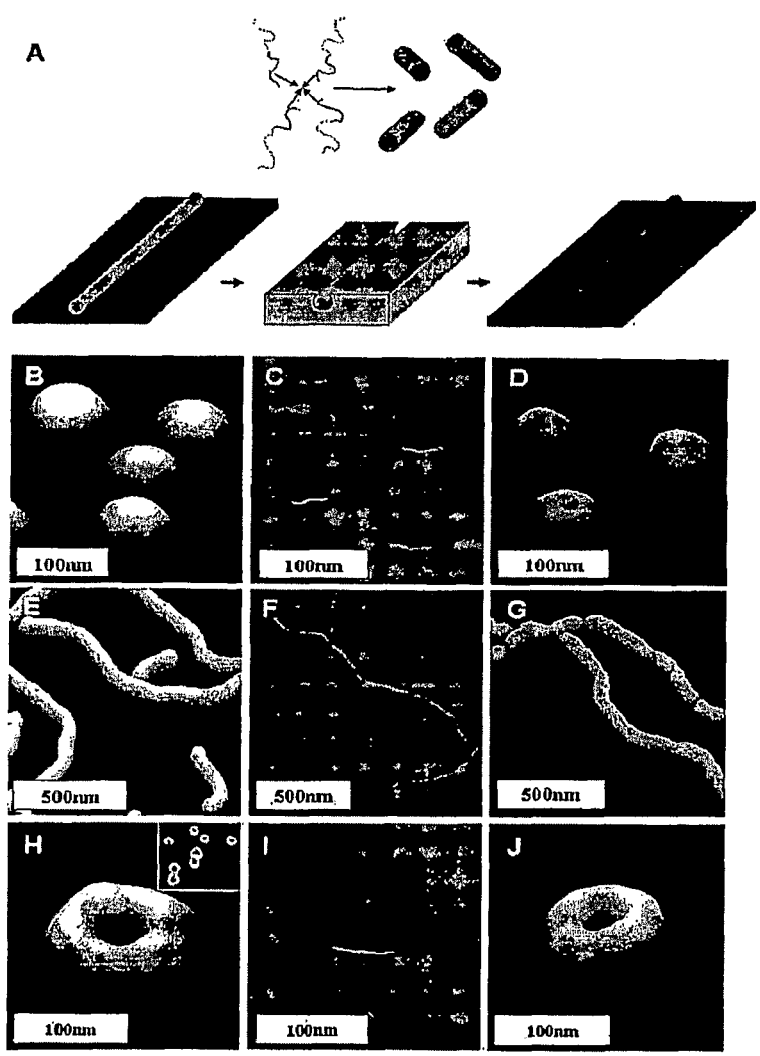
FIG. 8 shows an AFM images depicting PS-b-PI micelle replication according to an embodiment of the present invention.

Referring now to FIG. 8, earthworm hemoglobin protein was replicated using particle replication in non-wetting templates (PRINT). A template, or "master," for perfluoropolyether-dimethacrylate (PFPE-DMA) mold fabrication is generated by dispersing earthworm hemoglobin protein on a silicon wafer. This master can be used to template a surface nanostructure of the hemoglobin by pouring PFPE-DMA containing 1-hydroxycyclohexyl phenyl ketone over the patterned area of the master. The PFPE-DMA can then be cured and released from the master. Next, TMPTA is placed on a treated silicon wafer and the patterned PFPE mold placed on top of it. The entire apparatus is then subjected to a curing procedure and synthetic protein replicates are observed after separation of the PFPE mold and the treated silicon wafer using scanning electron microscopy (SEM) or transmission electron microscopy (TEM), as shown in FIG. 8.

Referring now to FIG. 8, AFM images depict PS-b-PI micelle replication according to embodiments of the present invention. Depending on the block-copolymer composition, self-assembly of PS-b-PI in heptane (a selective solvent for the PI block) results in micelles with well-defined shapes. FIG. 8A shows a schematic depicting self-assembly of micelles and their deposition onto substrates (brown/white), molding (green/black) and replication (blue/magenta). FIG. 8B shows a spherical micelle master, prepared by self-assembly of a 39 kDa-b-94 k Da PS-b-PI copolymer and solution deposition onto mica. FIG. 8C shows a PFPE mold of a spherical micelle master. FIG. 8D shows a triacrylate replica of spherical micelles. FIG. 8E shows a cylindrical micelle master, prepared by self-assembly of a 40 kDa-b-10 kDa PS-b-PI copolymer and solution deposition onto mica. FIG. 8F shows a PFPE mold of a cylindrical micelle master. FIG. 8G shows a triacrylate replica of cylindrical micelles. FIG. 8H shows a toroidal micelle master, prepared by self-assembly and deposition of a 21 kDa-b-4 kDa PS-b-PI copolymer and solution deposition onto mica; Inset: larger AFM image showing a collection of toroidal micelle nano-objects. FIG. 8I shows a PFPE mold of a toroidal micelle, and FIG. 8J shows a triacrylate replica of a toroidal micelle master.

Figure 9:
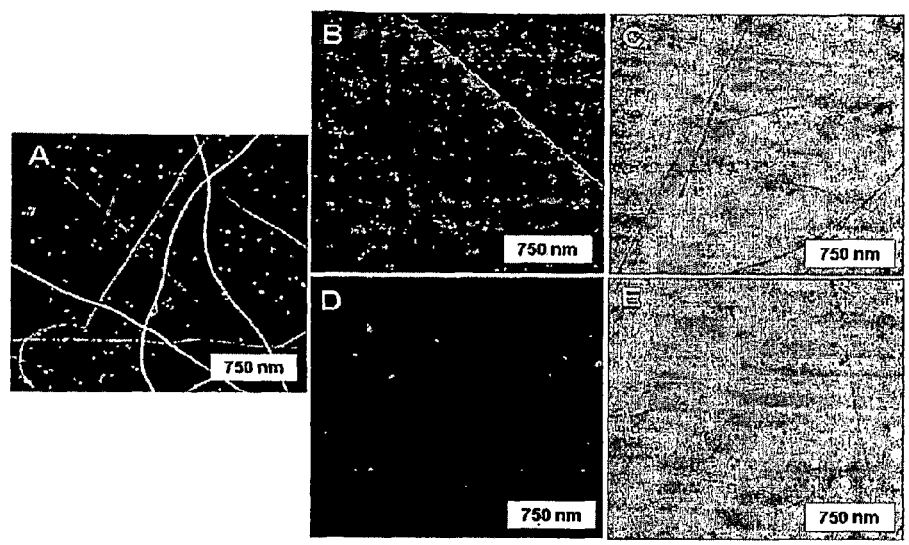
FIG. 9 shows replication of carbon nanotubes according to an embodiment of the present invention.

Referring now to FIG. 9, a replication of carbon nanotubes is shown replicated according to embodiments of the present invention. FIG. 9A shows an AFM image of a carbon nanotube master. FIG. 9B shows a PFPE mold of the nanotube master fabricated by photopolymerization of 1 kDa PFPE precursor. FIG. 9C shows a triacrylate replica derived from the 1 kDa PFPE mold. FIG. 9D shows a PFPE mold of the nanotube master fabricated by photopolymerization of 4 kDa PFPE precursor. And FIG. 9E shows a triacrylate replica derived from the 4 kDa PFPE mold.

In another aspect of the invention, a polymer system of the template for producing a continuous film by a roll-to-roll process includes a crosslinked perfluoropolyether such as, described herein and in U.S. Pat. No. 4,472,480; U.S. patent application Ser. No. 11/633,763; and also in references J. P. Rolland et al., J. Am. Chem. Soc., 126, 2322 (2004); A. Prioli et al. Macromol. Chem. Phys., 198, 1893 (1997); and J. P. Rolland et al., J. Am. Chem. Soc., 127, 10096 (2005), each of which is incorporated herein by reference in its entirety. The last reference notes the utility of crosslinked perfluoropolyethers as a templating method for formation of nanoparticles. This perfluoropolyether with vinyl end-groups is liquid and UV polymerizable/crosslinkable. When placed on nano-structured surfaces (with modest pressure optionally applied), the perfluoropolyether is able to replicate the surface and be polymerized/crosslinked in place. The low surface energy allows for easy removal and the low modulus allows for release from undercut morphologies. Various end-group chemistries of perfluoropolyethers can be employed including isocyanate termination which can be cured with various polyfunctional reactants (e.g. triols). Trialkyloxy end groups can also be considered for a sol-gel condensation crosslinking reaction to yield a material with useful properties.

Other variations of fluorocarbon elastomers can be employed for the template. Low molecular weight oligomers with functional end groups can be achieved using living free radical polymerization methods. The functional end groups can be modified with crosslinkable sites. Additionally, the fluorocarbon oligomers can be produced by either conventional or living free radical polymerization with functional monomers added for crosslinking reactions. The functional monomers can include at least one member selected from hydroxyethyl(meth)acrylate, (meth)acrylic acid, vinyl acetate (hydrolysis to yield vinyl alcohol), vinyl sulfonic acid, styrene sulfonic acid, 4-hydroxy styrene, 2-acrylamido-2-methyl propane sulfonate, maleic anhydride, glycidyl methacrylate, isocyanatoethyl methacrylate, combinations thereof, among others. The functional monomers can be employed directly in crosslinking reactions or further modified with other functional groups for crosslinking. Fluorocarbon monomers which can be employed in the oligomers noted supra can include at least one member selected from vinylidene fluoride, hexafluoropropylene, trifluorochloroethylene, tetrafluoroethylene, trifluoroethylene, fluorinated acrylates such as hexyluoro-iso-propyl(meth)acrylate, 1H,1H,3H-hexafluorobutyl(meth)acrylate, 1H,1H,5H-octafluoropentyl(meth)acrylate, pentafluorophenyl(meth)acrylate, perfluoro(methyl vinyl ether), combinations thereof, among others. Fluorinated acrylates such as those available from DuPont under the tradename Zonyl® are monomers of interest for the process of this invention. Other monomers can be included in amounts that do not adversely impact the desired properties.

Another aspect of the invention includes a method of forming the desired polymer template by polymerization of fluorinated monomers on the master template. The fluorinated monomers can include at least one member selected from vinylidene fluoride, hexafluoropropylene, trifluorochloroethylene, tetrafluoroethylene, trifluoroethylene, fluorinated acrylates such as hexyluoro-iso-propyl(meth)acrylate, 1H,1H,3H-hexafluorobutyl(meth)acrylate, 1H,1H,5H-octafluoropentyl(meth)acrylate, pentafluorophenyl(meth)acrylate, 1,1-dihydroperfluorobutyl(meth)acrylate, Zonyl® fluoroacrylate, combinations thereof, among others. In the case where these monomers are volatile, polymerization can be conducted at lower temperatures with UV or other forms of radiation (beta, gamma). Crosslinking monomers (such as diacrylates and divinylbenzene) can be incorporated to achieve the desired elastomeric template properties and employed for a roll-to-roll process employing a templated belt. The mechanical properties of high molecular weight versions of these materials can approach typical fluoroelastomer properties and, in some cases, be superior to the crosslinked oligomers noted above. If desired, relatively low viscosity monomers would be advantageous for patterning nanostructures. Monomers other than fluorinated monomers can be optionally employed such that they do not seriously compromise the required properties of low modulus, low surface energy and organic solvent/monomer resistance. Optionally, a combination of the monomers noted above and a polymer (normally the same structure as the monomers) dissolved in the monomers can be employed for the templating polymer to provide viscosity control and ease in the addition and polymerization of the templating polymer.

In specific cases, silicone rubber and various silicone based elastomers can be employed as the templating polymer. For monomers such as the acrylics and styrenics, in some cases, the solubility in the silicone elastomer may be too high to permit proper templating. However, with liquid oligomers and prepolymers, the solubility would be considerably lower and silicone based elastomers can be employed as the template.

Surfactants can be added to the oligomers, prepolymers or monomers employed for the template polymers described above. These surfactants can include acetylenic alcohols and diols as described in U.S. Pat. No. 5,789,505 and poly(propylene oxide) or poly(butylene oxide) based surfactants as described in U.S. Pat. No. 5,733,964, each of which are incorporated herein by reference in its entirety. Silicone based surfactants known in the art such as the silicone-poly(ethylene oxide) surfactants can also be considered. Fluorinated surfactants such as fluorinated hydrocarbons with sulfonic acid or carboxylic acid end or pendant groups (such as perfluorooctanoic acid and perfluorooctane sulfonic acid) can also be employed. The role of the surfactant will be to adjust the wetting characteristics of the template precursors such that they properly wet the nanostructured surface being templated.

IV. Materials

In one aspect of the invention, the templated polymers will be obtained from a liquid monomer or prepolymer and that are added to the template belt (or mold) and fill the nanostructured features of the template belt (or mold). Polymerization will be conducted and the resultant film/coating will be removed from the surface. One desirable polymer family for the film/coating will be (meth)acrylic based polymers. A large number of acrylate and methacrylate monomer variations exist of which many are commercially available.

The generalized poly(meth)acrylate structure is shown below with variants of R and R' given in the Table also shown below.

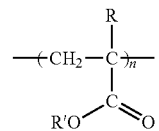

TABLE

| Methacrylates | Acrylates |
|---|---|
| PMMA R = —CH$_3$; R' = —CH$_3$ | PMA R = —H; R' = —CH$_3$ |
| PEMA R = —CH$_3$; R' = —CH$_2$CH | PEA R = —H; R' = —CH$_2$CH$_3$ |
| PnPMA R = —CH$_3$; | PnPA R = —H; |
| R' = —CH$_2$CH$_2$CH$_3$ | R' = —CH$_2$CH$_2$CH$_3$ |
| PiPMA R = —CH$_3$; R' = —CH(CH$_3$)$_2$ | PiPA R = —H; R' = —CH(CH$_3$)$_2$ |
| PnBMA R = —CH$_3$: | PnBA R = —H; |
| R' = —CH$_2$CH$_2$CH$_2$CH$_3$ | R' = —CH$_2$CH$_2$CH$_2$CH$_3$ |
| PtBMA R = —CH$_3$; R' = —C(CH$_3$)$_3$ | PtBA R = —H; R' = —C(CH$_3$)$_3$ |
| PnPrMA R = —CH$_3$ | PnPrA R = H |
| R' = —CH$_2$CH$_2$CH$_2$CH$_2$CH$_3$ | R' = —CH$_2$CH$_2$CH$_2$CH$_2$CH$_3$ |
| PMAA R = —CH$_3$; R' = —OH | PAA R = —H; R' = —OH |
| PEHMA R = —CH$_3$; | PEHA R = —H; |
| R' = —CH$_2$CH$_2$OH | R' = —CH$_2$CH$_2$OH |

Additional (meth)acrylates can be considered for the nanostructured films including at least one member selected from 2-ethyl hexyl(meth)acrylate, cyclohexyl(meth)acrylate, hexyluoro-iso-propyl(meth)acrylate, 1H,1H,3H-hexafluorobutyl(meth)acrylate, 1H,1H,5H-octafluoropentyl(meth)acrylate, pentafluorophenyl(meth)acrylate, 2,2,2-trifluoroethyl(meth)acrylate, 1,1-dihydroperfluorobutyl(meth)acrylate (e.g., including perfluoroacrylate monomer mixtures such as Zonyl® TA-N), and combinations thereof, among others. The (meth)acrylates can also be copolymerized with other monomers such as styrene, acrylonitrile, maleic anhydride and vinyl pyrrolidone. Crosslinking monomers such as di(meth)acrylates and divinyl benzene will be optionally added to improve performance. In the case of low Tg (meth)acrylates, crosslinking will be required to maintain dimensional stability after fabrication and in application use.

Polystyrene and styrene copolymers can also be considered for the nanostructured films of this invention. Styrene copolymers can include the (meth)acrylates noted above, acrylonitrile, maleic anhydride, vinyl pyrrolidone, and α-methyl styrene, Unsaturated polyesters are based on mixtures of oligomeric polyesters containing double bonds with styrene monomer. These systems are normally liquid and also can used for making the nanostructured films of the invention. Polymers based on vinyl acetate such as poly(vinyl acetate), vinyl acetate/(meth)acrylate copolymers, and vinyl acetate/vinyl pyrrolidone copolymers can also be considered.

Ring opening polymerizations such as the anionic polymerization of ε-caprolactam to yield nylon 6 and the ring opening polymerization of ε-caprolactone to yield poly(ε-caprolactone) can also be employed for making the nanostructured film.

Thermosetting liquid systems such as RTV silicones, epoxies, vinyl esters, combinations thereof, among others systems can also be employed as the nanostructured films/coatings for the applications of this invention. If desired, an article can be produced by the inventive process that includes a plurality of films or layers.

Fluorinated monomers in addition to the fluorinated acrylates noted above can include vinylidene fluoride, tetrafluoroethylene, fluorinated vinyl ether, trifluoroethylene, hexafluoropropylene, trifluorochloroethylene, combinations thereof, among others. In the case of volatile fluorinated monomers, low temperature are typically employed to yield the desired conversion of liquid monomers to polymers and radiation techniques such as UV, gamma or beta radiation can be employed. Copolymers containing these fluoropolymers can include acrylates and styrenics.

High polarity monomers including monomers yielding water soluble polymers can be used in the inventive process. In specific cases, it may be desired to have the nanostructured surfaces offering hydrogel-like properties thus crosslinking agents (e.g. divinyl benzene, di(meth)acrylates) can be incorporated in the monomer system. While any suitable crosslinking agent can be employed, examples of suitable agents include at least one member selected from acrylonitrile, acrylamide, N,N-dimethyl acrylamide, (meth)acrylic acid, styrene sulfonic acid, N-vinyl formamide, N-vinyl acetamide, vinyl methyl ether, N-vinyl pyrrolidone, 4-vinyl pyridine, among others.

Functional oligomers with chain extenders or crosslinking agents can be employed as the polymer to be templated by this process. Hydroxyl terminated polyether and polyester oligomers (e.g. poly(ethylene oxide), poly(propylene oxide), poly(tetramethylene oxide), poly(ε-caprolactone) and polyesters based on aliphatic dicarboxylic acids and aliphatic diols) can be employed with addition of diisocyanates.

Liquid vinyl plastisols based on PVC particles suspended in plasticizer can be employed for these surfaces where the PVC particle diameters are lower or in the range of the desired dimensions. Heat treatment of the suspension can allow for dissolution and flow into the nano-dimension crevices of the template.

Inorganic polymers such as silica derived from tetraalkoxysilane can be employed as the templated polymer. As an example, tetraethyloxysilane (TEOS) can be added to the template surface and polymerized (acid catalyst or heat). In cases wherein the resultant silica would be too brittle to be handled as a continuous film, a laminate layer either polymerized on top of the silica or polymer film with enhanced biomedical characteristics can be employed to bond to the silica layer and allow removal from the template surface. Other inorganic sol-gel systems includes titania, zirconia, among other similar based precursors. Organic-inorganic sol-gel systems such as epoxy and urethane based hybrids can be employed. A specific example can involve TEOS, 3-aminopropyltriethyoxysilane and the diglycidyl ether of Bisphenol A which with condensation will yield an epoxy-silica hybrid.

A wide range of liquid oligomers or prepolymers can be employed as the templated polymer of this invention. The polymerization process employed can be chosen such that covalent bonding to the template does not occur to an extent such that the templated polymer is difficult or possible to remove. Optionally, monomers such as those noted above can be combined with a polymer (a desirable polymer would include the same monomer(s)) in a solution to be used as the templated polymer once polymerization is completed. This would allow control of viscosity, shrinkage and other polymerization variables.

The templated polymer can be formed from a polymer solution applied to the surface of the templating polymer negative. Upon devolatilization of the solution, the surface features will duplicate the original master template. This may require procedures such that the polymer will properly flow into the crevices of the nanostructures. This can include heat treatment to allow for polymer flow, choice of an excellent film forming polymer, controlled devolatilization rates to facilitate polymer flow into the structure. Alternatively polymer emulsions and dispersions of film forming polymer can be added to the surface of the templating polymer negative to yield the desired surface upon removal of the volatile carrier (e.g. water) of the emulsion or dispersion.

In certain embodiments, the present invention broadly describes and employs solvent resistant, low surface energy polymeric materials for fabricating articles or articles, such as molds having micro- and/or nano-sized cavities. According to some embodiments the low surface energy polymeric materials include, but are not limited to fluoropolyether or perfluoropolyether (collectively "PFPE"), poly(dimethylsiloxane) (PDMS), poly(tetramethylene oxide), polyethylene oxide), poly(oxetanes), polyisoprene, polybutadiene, fluoroolefin-based fluoroelastomers, and the like. An example of forming a mold of a nanostructured surface with such materials includes casting liquid PFPE precursor materials onto a substrate (or master) and then curing the liquid PFPE precursor materials to generate a replica pattern of the master. For simplification purposes, most of the description will focus on PFPE materials, however, it will be appreciated that other polymers, such as those recited herein, can be applied to the methods, materials, and articles of the present invention.

According to certain embodiments of the present invention, "curing" a liquid polymer, for example a liquid PFPE precursor, means transforming the polymer from a liquid state to a non-liquid state (excluding a gas state) such that the polymer does not readily flow, such as a material with a relatively high viscosity or a rubbery state. In some embodiments, the non-liquid state that the polymer is transformed to is a gel state. In some embodiments, the polymer in the non-liquid state can include un-reacted polymerizable groups. In other embodiments, the polymer liquid precursor is capable of undergoing a first cure to become non-liquid such that the polymer becomes not fully soluble in a solvent. In other embodiments, when the liquid polymer precursor is cured it is meant that the polymer has transitioned into a non-liquid polymer that forms fibers about an object drawn through the material. In other embodiments, an initial cure of the liquid polymer precursor transitions the polymer to a non-conformable state at room temperature. In other embodiments, following a cure, the polymer takes a gel form, wherein gel means an article that is free-standing or self-supporting in that its yield value is greater than the shear stress imposed by gravity.

Representative solvent resistant elastomer-based materials include but are not limited to fluorinated elastomer-based materials. As used herein, the term "solvent resistant" refers to a material, such as an elastomeric material that does not substantially swell or dissolve in common hydrocarbon-based organic solvents or acidic or basic aqueous solutions. Representative fluorinated elastomer-based materials include but are not limited to fluoropolyether and perfluoropolyether (collectively "PFPE") based materials.

The properties of these materials can be tuned over a wide range through the judicious choice of additives, fillers, reactive co-monomers, and functionalization agents, examples of which are described further herein. Such properties that are desirable to modify, include, but are not limited to, modulus, tear strength, surface energy, permeability, functionality, mode of cure, solubility, toughness, hardness, elasticity, swelling characteristics, absorption, adsorption, combinations thereof, and the like. Some examples of methods of adjusting mechanical and or chemical properties of the finished material includes, but are not limited to, shortening the molecular weight between cross-links to increase the modulus of the material, adding monomers that form polymers of high Tg to increase the modulus of the material, adding charged monomer or species to the material to increase the surface energy or wetability of the material, combinations thereof, and the like.

According to one embodiment, materials for use herein (e.g., PFPE materials) have surface energy below about 30 mN/m. According to another embodiment the surface energy is between about 7 mN/m and about 20 mN/m. According to a more preferred embodiment, the surface energy is between about 10 mN/m and about 15 mN/m. The non-swelling nature and easy release properties of the presently disclosed materials (e.g. PFPE materials) allow for the fabrication of laminate articles.

In some embodiments the liquid PFPE precursor includes a chain extended material such that two or more chains are linked together before adding polymerizablable groups. Accordingly, in some embodiments, a "linker group" joins two chains to one molecule. In some embodiments, as shown in Scheme 1, the linker group joins three or more chains.

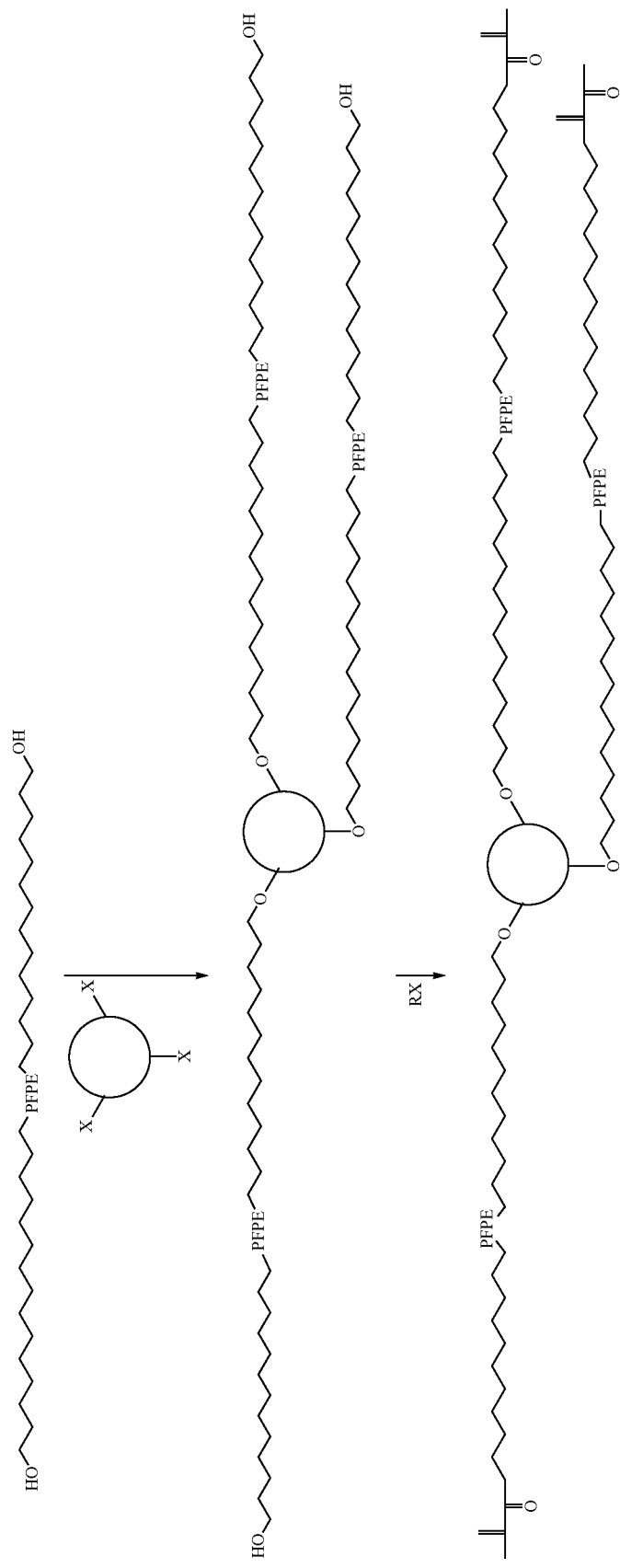
Scheme 1. Linker group joining three PFPE chains.

In some embodiments, X is selected from the group including, but not limited to an isocyanate, an acid chloride, an epoxy, and a halogen. In some embodiments, R is selected from the group including, but not limited to an acrylate, a methacrylate, a styrene, an epoxy, a carboxylic, an anhydride, a maleimide, an isocyanate, an olefinic, and an amine. In some embodiments, the circle represents any multifunctional molecule. In some embodiments, the multifunctional molecule includes a cyclic molecule. PFPE refers to any PFPE material provided herein.

In some embodiments the PFPE liquid precursor is encapped with an epoxy moiety that can be photocured using a photoacid generator. Photoacid generators suitable for use in the presently disclosed subject matter include, but are not limited to: bis(4-tert-butylphenyl)iodonium p-toluenesulfonate, bis(4-tert-butylphenyl)iodonium triflate, (4-bromophenyl)diphenylsulfonium triflate, (tart-butoxycarbonylmethoxynaphthyl)-diphenylsulfonium triflate, (tert-butoxycarbonylmethoxyphenyl)diphenylsulfonium triflate, (4-tert-butylphenyl)diphenylsulfonium triflate, (4-chlorophenyl)diphenylsulfonium triflate, diphenyliodonium-9,10-dimethoxyanthracene-2-sulfonate, diphenyliodonium hexafluorophosphate, diphenyliodonium nitrate, diphenyliodonium perfluoro-1-butanesulfonate, diphenyliodonium p-toluenesulfonate, diphenyliodonium triflate, (4-fluorophenyl)diphenylsulfonium triflate, N-hydroxynaphthalimide triflate, N-hydroxy-5-norbornene-2,3-dicarboximide perfluoro-1-butanesulfonate, N-hydroxyphthalimide triflate, [4-[(2-hydroxytetradecyl)oxy]phenyl]phenyliodonium hexafluoroantimonate, (4-iodophenyl)diphenylsulfonium triflate, (4-methoxyphenyl)diphenylsulfonium triflate, 2-(4-methoxystyryl)-4,6-bis(trichloromethyl)-1,3,5-triazine, (4-methylphenyl)diphenylsulfonium triflate, (4-methylthiophenyl)methyl phenyl sulfonium triflate, 2-naphthyl diphenylsulfonium triflate, (4-phenoxyphenyl)diphenylsulfonium triflate, (4-phenylthiophenyl)diphenylsulfonium triflate, thiobis(triphenyl sulfonium hexafluorophosphate), triarylsulfonium hexafluoroantimonate salts, triarylsulfonium hexafluorophosphate salts, triphenylsulfonium perfluoro-1-butanesulfonate, triphenylsulfonium triflate, tris(4-tert-butylphenyl)sulfonium perfluoro-1-butanesulfonate, and tris(4-tert-butylphenyl)sulfonium triflate.

In some embodiments the liquid PFPE precursor cures into a highly UV and/or highly visible light transparent elastomer. In some embodiments the liquid PFPE precursor cures into an elastomer that is highly permeable to oxygen, carbon dioxide, and nitrogen, a property that can facilitate maintaining the viability of biological fluids/cells disposed therein. In some embodiments, additives are added or layers are created to enhance the barrier properties of the articles to molecules, such as oxygen, carbon dioxide, nitrogen, dyes, reagents, and the like.

In some embodiments, the material suitable for use with the presently disclosed subject matter includes an acrylate material having a fluorinated acrylate or a fluorinated methacrylate having the following structure:

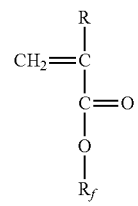

wherein:

R is selected from the group including, but not limited to H, alkyl, substituted alkyl, aryl, and substituted aryl; and $R_f$ includes a fluoroalkyl chain with a —$CH_2$— or a —$CH_2$—$CH_2$— spacer between a perfluoroalkyl chain and the ester linkage. In some embodiments, the perfluoroalkyl group has hydrogen substituents.

According to an alternative embodiment, the PFPE material includes a urethane block as described and shown in the following structures provided in Scheme 2:

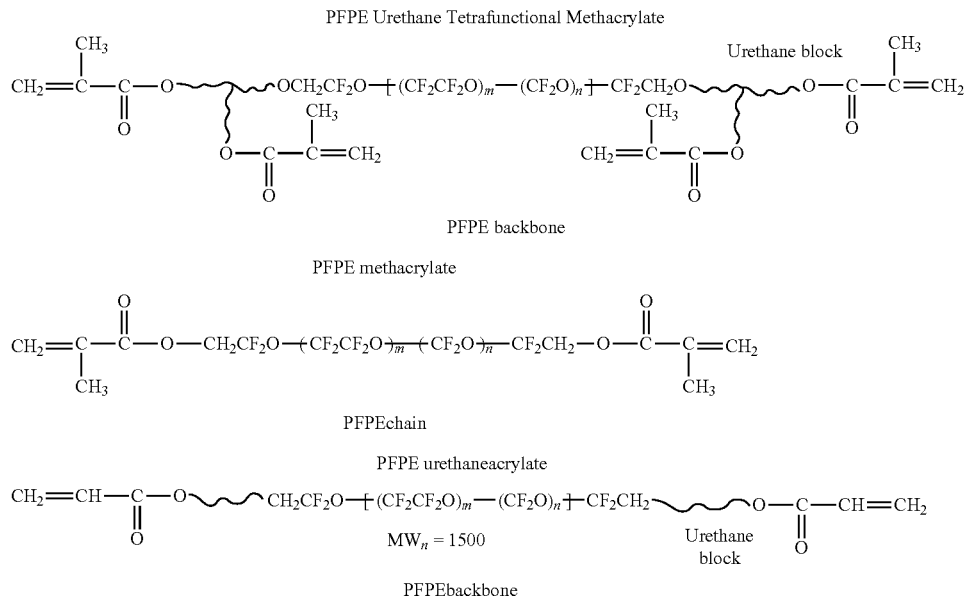

According to an embodiment of the present invention, PFPE urethane tetrafunctional methacrylate materials such as the above described can be used as the materials and methods of the present invention or can be used in combination with other materials and methods described herein, as will be appreciated by one of ordinary skill in the art.

Scheme 3. PFPE Urethane Systems
According to some embodiments, urethane systems include materials with the following structures.
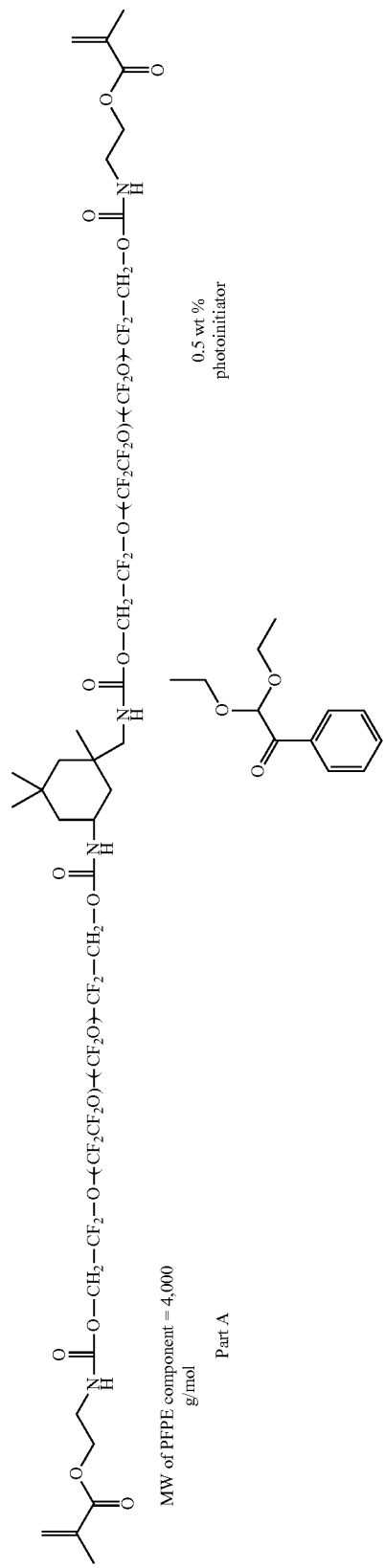
MW of PFPE component = 4,000 g/mol
Part A
0.5 wt % photoinitiator
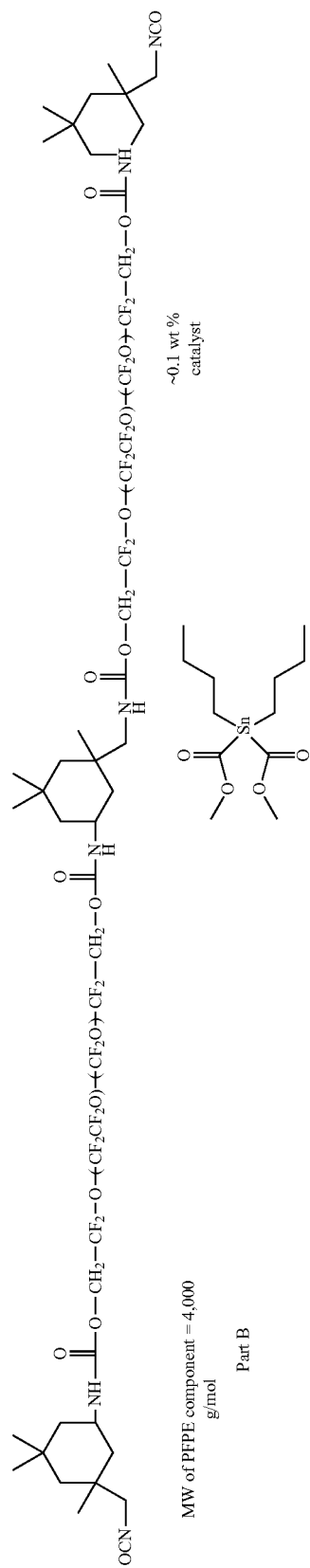
MW of PFPE component = 4,000 g/mol
Part B
~0.1 wt % catalyst -continued
MW of PFPE component = 2,000 g/mol
Part C
Part D
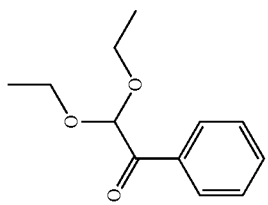

According to this scheme, part A is a UV curable precursor and parts B and C make up a thermally curable component of the urethane system. The fourth component, part D, is an end-capped precursor, (e.g., styrene end-capped liquid precursor). According to some embodiments, part D reacts with latent methacrylate, acrylate, or styrene groups contained in a base material, thereby adding chemical compatibility or a surface passivation to the base material and increasing the functionality of the base material.

IV.A. Fluoroolefin-Based Materials

Further, in some embodiments, the materials used herein are selected from highly fluorinated fluoroelastomers, e.g., fluoroelastomers having at least fifty-eight weight percent fluorine, as described in U.S. Pat. No. 6,512,063 to Tang, which is incorporated herein by reference in its entirety. Such fluoroelastomers can be partially fluorinated or perfluorinated and can contain between 25 to 70 weight percent, based on the weight of the fluoroelastomer, of copolymerized units of a first monomer, e.g., vinylidene fluoride ($VF_2$) or tetrafluoroethylene (TFE). The remaining units of the fluoroelastomers include one or more additional copolymerized monomers, that are different from the first monomer, and are selected from the group including, but not limited to fluorine-containing olefins, fluorine containing vinyl ethers, hydrocarbon olefins, and combinations thereof.

These fluoroelastomers include VITON® (DuPont Dow Elastomers, Wilmington, Del., United States of America) and Kel-F type polymers, as described in U.S. Pat. No. 6,408,878 to Unger et al. These commercially available polymers, however, have Mooney viscosities ranging from about 40 to 65 (ML 1+10 at 121° C.) giving them a tacky, gum-like viscosity. When cured, they become a stiff, opaque solid. As currently available, VITON® and Kel-F have limited utility for microscale molding. Curable species of similar compositions, but having lower viscosity and greater optical clarity, is needed in the art for the applications described herein. A lower viscosity (e.g., 2 to 32 (ML 1+10 at 121° C.)) or more preferably as low as 80 to 2000 cSt at 20° C., composition yields a pourable liquid with a more efficient cure.

More particularly, the fluorine-containing olefins include, but are not limited to, vinylidine fluoride, hexafluoropropylene (HFP), tetrafluoroethylene (TFE), 1,2,3,3,3-pentafluoropropene (1-HPFP), chlorotrifluoroethylene (CTFE) and vinyl fluoride.

The fluorine-containing vinyl ethers include, but are not limited to perfluoro(alkyl vinyl)ethers (PAVEs). More particularly, perfluoro(alkyl vinyl) ethers for use as monomers include perfluoro(alkyl vinyl)ethers of the following formula:

$$CF_2=CFO(R_fO)_n(R_fO)_mR_f$$

wherein each $R_f$ is independently a linear or branched $C_1$-$C_6$ perfluoroalkylene group, and m and n are each independently an integer from 0 to 10.

In some embodiments, the perfluoro(alkyl vinyl)ether includes a monomer of the following formula:

$$CF_2=CFO(CF_2CFXO)_nR_f$$

wherein X is F or $CF_3$, n is an integer from 0 to 5, and $R_f$ is a linear or branched $C_1$-$C_6$ perfluoroalkylene group. In some embodiments, n is 0 or 1 and $R_f$ includes 1 to 3 carbon atoms. Representative examples of such perfluoro(alkyl vinyl) ethers include perfluoro(methyl vinyl)ether (PMVE) and perfluoro(propyl vinyl) ether (PPVE).

In some embodiments, the perfluoro(alkyl vinyl)ether includes a monomer of the following formula:

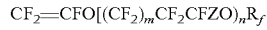

wherein $R_f$ is a perfluoroalkyl group having 1-6 carbon atoms, m is an integer from 0 or 1, n is an integer from 0 to 5, and Z is F or $CF_3$. In some embodiments, $R_f$ is $C_3F_7$, m is 0, and n is 1.

In some embodiments, the perfluoro(alkyl vinyl)ether monomers include compounds of the formula:

$$CF_2=CFO[(CF_2CF\{CF_3\}O)_n(CF_2CF_2CF_2O)_m(CF2)_p]C_xF_{2x+1}$$

wherein m and n each integers independently from 0 to 10, p is an integer from 0 to 3, and x is an integer from 1 to 5. In some embodiments, n is 0 or 1, m is 0 or 1, and x is 1.

Other examples of useful perfluoro(alkyl vinyl ethers) include:

$$CF_2=CFOCF_2CF(CF_3)O(CF_2O)_mC_nF_{2n+1}$$

wherein n is an integer from 1 to 5, m is an integer from 1 to 3. In some embodiments, n is 1.

In embodiments wherein copolymerized units of a perfluoro(alkyl vinyl) ether (PAVE) are present in the presently described fluoroelastomers, the PAVE content generally ranges from 25 to 75 weight percent, based on the total weight of the fluoroelastomer. If the PAVE is perfluoro(methyl vinyl) ether (PMVE), then the fluoroelastomer contains between 30 and 55 wt. % copolymerized PMVE units.

Hydrocarbon olefins useful in the presently described fluoroelastomers include, but are not limited to ethylene (E) and propylene (P). In embodiments wherein copolymerized units of a hydrocarbon olefin are present in the presently described fluoroelastomers, the hydrocarbon olefin content is generally 4 to 30 weight percent.

Further, the presently described fluoroelastomers can, in some embodiments, include units of one or more cure site monomers. Examples of suitable cure site monomers include: i) bromine-containing olefins; ii) iodine-containing olefins; iii) bromine-containing vinyl ethers; iv) iodine-containing vinyl ethers; v) fluorine-containing olefins having a nitrile group; vi) fluorine-containing vinyl ethers having a nitrile group; vii) 1,1,3,3,3-pentafluoropropene (2-HPFP); viii) perfluoro(2-phenoxypropyl vinyl)ether; and ix) non-conjugated dienes.

In certain embodiments, the brominated cure site monomers can contain other halogens, preferably fluorine. Examples of brominated olefin cure site monomers are $CF_2=CFOCF_2CF_2CF_2OCF_2CF_2Br$; bromotrifluoroethylene; 4-bromo-3,3,4,4-tetrafluorobutene-1 (BTFB); and others such as vinyl bromide, 1-bromo-2,2-difluoroethylene; perfluoroailyl bromide; 4-bromo-1,1,2-trifluorobutene-1; 4-bromo-1,1,3,3,4,4,-hexafluorobutene; 4-bromo-3-chloro-1,1,3,4,4-pentafluorobutene; 6-bromo-5,5,6,6-tetrafluorohexene; 4-bromoperfluorobutene-1 and 3,3-difluoroallyl bromide. Brominated vinyl ether cure site monomers include 2-bromo-perfluoroethyl perfluorovinyl ether and fluorinated compounds of the class $CF_2Br-R_f-O-CF=CF_2$ (wherein $R_f$ is a perfluoroalkylene group), such as $CF_2BrCF_2O-CF=CF_2$, and fluorovinyl ethers of the class $ROCF=CFBr$ or $ROCBr=CF_2$ (wherein R is a lower alkyl group or fluoroalkyl group), such as $CH_3OCF=CFBr$ or $CF_3CH_2OCF=CFBr$.

Suitable iodinated cure site monomers include iodinated olefins of the formula: $CHR=CH-Z-CH_2CHR-I$, wherein R is $-H$ or $-CH_3$; Z is a $C_1$ to $C_{18}$ (per)fluoroalkylene radical, linear or branched, optionally containing one or more ether oxygen atoms, or a (per)fluoropolyoxyalkylene radical as disclosed in U.S. Pat. No. 5,674,959. Other examples of useful iodinated cure site monomers are unsaturated ethers of the formula: $I(CH_2CF_2CF_2)_nOCF=CF_2$ and ICH$_2$CF$_2$O[CF(CF$_3$)CF$_2$O]$_n$CF=CF$_2$, and the like, wherein n is an integer from 1 to 3, such as disclosed in U.S. Pat. No. 5,717,036. In addition, suitable iodinated cure site monomers including iodoethylene, 4-iodo-3,3,4,4-tetrafluorobutene-1 (ITFB); 3-chloro-4-iodo-3,4,4-trifluorobutene; 2-iodo-1,1,2,2-tetrafluoro-1-(vinyloxy)ethane; 2-iodo-1-(perfluorovinyloxy)-1,1,-2,2-tetrafluoroethylene; 1,1,2,3,3,3-hexafluoro-2-iodo-1-(perfluorovinyloxy)propane; 2-iodoethyl vinyl ether; 3,3,4,5,5,5-hexafluoro-4-iodopentene; and iodotrifluoroethylene are disclosed in U.S. Pat. No. 4,694,045. Allyl iodide and 2-iodo-perfluoroethyl perfluorovinyl ether also are useful cure site monomers.

Useful nitrile-containing cure site monomers include, but are not limited to those of the formulas shown below:

CF$_2$=CF—O(CF$_2$)$_n$—CN wherein n is an integer from 2 to 12. In some embodiments, n is an integer from 2 to 6.

CF$_2$=CF—O[CF$_2$—CF(CF)—O]$_n$—CF$_2$—CF(CF$_3$)—CN wherein n is an integer from 0 to 4. In some embodiments, n is an integer from 0 to 2.

CF$_2$=CF—[OCF$_2$CF(CF$_3$)]$_x$—O—(CF$_2$)$_n$—CN wherein x is 1 or 2, and n is an integer from 1 to 4; and CF$_2$=CF—O—(CF$_2$)$_n$—O—CF(CF$_3$)—CN wherein n is an integer from 2 to 4. In some embodiments, the cure site monomers are perfluorinated polyethers having a nitrile group and a trifluorovinyl ether group.

In some embodiments, the cure site monomer is:

CF$_2$=CFOCF$_2$CF(CF$_3$)OCF$_2$CF$_2$CN i.e., perfluoro(8-cyano-5-methyl-3,6-dioxa-1-octene) or 8-CNVE.

Examples of non-conjugated diene cure site monomers include, but are not limited to 1,4-pentadiene; 1,5-hexadiene; 1,7-octadiene; 3,3,4,4-tetrafluoro-1,5-hexadiene; and others, such as those disclosed in Canadian Patent No. 2,067,891 and European Patent No. 0784064A1. A suitable triene is 8-methyl-4-ethylidene-1,7-octadiene.

In embodiments wherein the fluoroelastomer will be cured with peroxide, the cure site monomer is preferably selected from the group including, but not limited to 4-bromo-3,3,4,4-tetrafluorobutene-1 (BTFB); 4-iodo-3,3,4,4-tetrafluorobutene-1 (ITFB); allyl iodide; bromotrifluoroethylene and 8-CNVE. In embodiments wherein the fluoroelastomer will be cured with a polyol, 2-HPFP or perfluoro(2-phenoxypropyl vinyl)ether is the preferred cure site monomer. In embodiments wherein the fluoroelastomer will be cured with a tetraamine, bis(aminophenol) or bis(thioaminophenol), 8-CNVE is the preferred cure site monomer.

Units of cure site monomer, when present in the presently disclosed fluoroelastomers, are typically present at a level of 0.05-10 wt. % (based on the total weight of fluoroelastomer), preferably 0.05-5 wt. % and most preferably between 0.05 and 3 wt. %.

Fluoroelastomers which can be used in the presently disclosed subject matter include, but are not limited to, those having at least 58 wt. % fluorine and having copolymerized units of i) vinylidene fluoride and hexafluoropropylene; ii) vinylidene fluoride, hexafluoropropylene and tetrafluoroethylene; iii) vinylidene fluoride, hexafluoropropylene, tetrafluoroethylene and 4-bromo-3,3,4,4-tetrafluorobutene-1; iv) vinylidene fluoride, hexafluoropropylene, tetrafluoroethylene and 4-iodo-3,3,4,4-tetrafluorobutene-1; v) vinylidene fluoride, perfluoro(methyl vinyl)ether, tetrafluoroethylene and 4-bromo-3,3,4,4-tetrafluorobutene-1; vi) vinylidene fluoride, perfluoro(methyl vinyl)ether, tetrafluoroethylene and 4-iodo-3,3,4,4-tetrafluorobutene-1; vii) vinylidene fluoride, perfluoro(methyl vinyl)ether, tetrafluoroethylene and 1,1,3,3,3-pentafluoropropene; viii) tetrafluoroethylene, perfluoro(methyl vinyl)ether and ethylene; ix) tetrafluoroethylene, perfluoro(methyl vinyl)ether, ethylene and 4-bromo-3,3,4,4-tetrafluorobutene-1; x) tetrafluoroethylene, perfluoro(methyl vinyl)ether, ethylene and 4-iodo-3,3,4,4-tetrafluorobutene-1; xi) tetrafluoroethylene, propylene and vinylidene fluoride; xii) tetrafluoroethylene and perfluoro(methyl vinyl)ether; xiii) tetrafluoroethylene, perfluoro(methyl vinyl)ether and perfluoro(8-cyano-5-methyl-3,6-dioxa-1-octene); xiv) tetrafluoroethylene, perfluoro(methyl vinyl)ether and 4-bromo-3,3,4,4-tetrafluorobutene-1; xv) tetrafluoroethylene, perfluoro(methyl vinyl)ether and 4-iodo-3,3,4,4-tetrafluorobutene-1; and xvi) tetrafluoroethylene, perfluoro(methyl vinyl)ether and perfluoro(2-phenoxypropyl vinyl) ether.

Additionally, iodine-containing endgroups, bromine-containing endgroups or combinations thereof can optionally be present at one or both of the fluoroelastomer polymer chain ends as a result of the use of chain transfer or molecular weight regulating agents during preparation of the fluoroelastomers. The amount of chain transfer agent, when employed, is calculated to result in an iodine or bromine level in the fluoroelastomer in the range of 0.005-5 wt. %, preferably 0.05-3 wt. %.

Examples of chain transfer agents include iodine-containing compounds that result in incorporation of bound iodine at one or both ends of the polymer molecules. Methylene iodide; 1,4-diiodoperfluoro-n-butane; and 1,6-diiodo-3,3,4,4-tetrafluorohexane are representative of such agents. Other iodinated chain transfer agents include 1,3-diiodoperfluoropropane; 1,6-diiodoperfluorohexane; 1,3-diiodo-2-chloroperfluoropropane; 1,2-di(iododifluoromethyl)perfluorocyclobutane; monoiodoperfluoroethane; monoiodoperfluorobutane; 2-iodo-1-hydroperfluoroethane, and the like. Also included are the cyano-iodine chain transfer agents disclosed European Patent No. 0868447A1. Particularly preferred are diiodinated chain transfer agents.

Examples of brominated chain transfer agents include 1-bromo-2-iodoperfluoroethane; 1-bromo-3-iodoperfluoropropane; 1-iodo-2-bromo-1,1-difluoroethane and others such as disclosed in U.S. Pat. No. 5,151,492.

Other chain transfer agents suitable for use include those disclosed in U.S. Pat. No. 3,707,529, which is incorporated herein by reference in its entirety. Examples of such agents include isopropanol, diethylmalonate, ethyl acetate, carbon tetrachloride, acetone and dodecyl mercaptan.

IV.B. Dual Photo-Curable and Thermal-Curable Materials

According to other embodiments of the present invention, a dual cure material includes one or more of a photo-curable constituent and a thermal-curable constituent. In one embodiment, the photo-curable constituent is independent from the thermal-curable constituent such that the material can undergo multiple cures. A material having the ability to undergo multiple cures is useful, for example, in forming layered articles or in connecting or attaching articles to other articles or portions or components of articles to other portions or components of articles. For example, a liquid material having photocurable and thermal-curable constituents can undergo a first cure to form a first article through, for example, a photocuring process or a thermal curing process. Then the photocured or thermal cured first article can be adhered to a second article of the same material or any material similar thereto that will thermally cure or photocure and bind to the material of the first article. By positioning the first article and second article adjacent one another and subjecting the first and second articles to a thermal curing or photocuring, whichever component that was not activated on the first curing. Thereafter, either the thermal cure constituents of the first article that were left un-activated by the photocuring process or the photocure constituents of the first article that were left un-activated by the first thermal curing, will be activated and bind the second article. Thereby, the first and second articles become adhered together. It will be appreciated by one of ordinary skill in the art that the order of curing processes is independent and a thermal-curing can occur first followed by a photocuring or a photocuring can occur first followed by a thermal curing.

According to yet another embodiment, dual cure materials can include multiple thermo-curable constituents included in the material such that the material can be subjected to multiple independent thermal-cures. For example, the multiple thermal-curable constituents can have different activation temperature ranges such that the material can undergo a first thermal-cure at a first temperature range and a second thermal-cure at a second temperature range. Accordingly, the material can be adhered to multiple other materials through different thermal-cures, thereby, forming a multiple laminate layer article.

According to another embodiment, dual cure materials can include materials having multiple photo curable constituents that can be triggered at different wavelengths. For example, a first photo curable constituent can be triggered at a first applied wavelength and such wavelength can leave a second photo curable constituent available for activation at a second wavelength.

Examples of chemical groups which would be suitable end-capping agents for a UV curable component include: methacrylates, acrylates, styrenics, epoxides, cyclobutanes and other 2+2 cycloadditions, combinations thereof, and the like. Examples of chemical group pairs which are suitable to endcap a thermally curable component include: epoxy/amine, epoxy/hydroxyl, carboxylic acid/amine, carboxylic acid/hydroxyl, ester/amine, ester/hydroxyl, amine/anhydride, acid halide/hydroxyl, acid halide/amine, amine/halide, hydroxyl/halide, hydroxyl/chlorosilane, azide/acetylene and other so-called "click chemistry" reactions, and metathesis reactions involving the use of Grubb's-type catalysts, combinations thereof, and the like.

The presently disclosed methods for the adhesion of multiple layers of an article to one another or to a separate surface can be applied to PFPE-based materials, as well as a variety of other materials, including PDMS and other liquid-like polymers. Examples of liquid-like polymeric materials that are suitable for use in the presently disclosed adhesion methods include, but are not limited to, PDMS, poly(tetramethylene oxide), poly(ethylene oxide), poly(oxetanes), polyisoprene, polybutadiene, and fluoroolefin-based fluoroelastomers, such as those available under the registered trademarks VITON® AND KALREZ®.

Accordingly, the presently disclosed methods can be used to adhere layers of different polymeric materials together to form articles, such as laminate molds, and the like.

IV.C. Phosphazene-Containing Polymers

According to some embodiments, articles and methods disclosed herein can be formed with materials that include phosphazene-containing polymers having the following structure. According to these embodiments, R, in the structure below, can be a fluorine-containing alkyl chain. Examples of such fluorine-containing alkyl chains can be found in *Langmuir*, 2005, 21, 11604, the disclosure of which is incorporated herein by reference in its entirety. The articles disclosed in this application can be formed from phosphazene-containing polymers or from PFPE in combination with phosphazene-containing polymers.

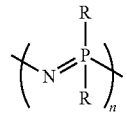

IV.D. Materials End-Capped with an Aryl Trifluorovinyl Ether (TVE)

In some embodiments, articles and methods disclosed herein can be formed with materials that include materials end-capped with one or more aryl trifluorovinyl ether (TVE) group, as shown in the structure below. Examples of materials end-capped with a TVE group can be found in *Macromolecules*, 2003, 36, 9000, which is incorporated herein by reference in its entirety. These structures react in a 2+2 addition at about 150° C. to form perfluorocyclobutyl moieties. In some embodiments, Rf can be a PFPE chain. In some embodiments three or more TVE groups are present on a 3-armed PFPE polymer such that the material crosslinks into a network.

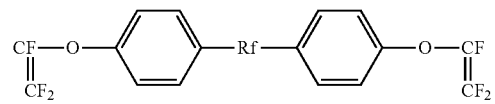

IV.E. Sodium Naphthalene Etchant

In some embodiments a sodium naphthalene etchant, such as commercially available TETRAETCH™, is contacted with a layer of a fluoropolymer article, such as an article disclosed herein. In other embodiments, a sodium naphthalene etchant is contacted with a layer of a PFPE-based article, such as laminate articles disclosed herein. According to such embodiments, the etch reacts with C—F bonds in the polymer of the article forming functional groups along a surface of the article. In some embodiments, these functional groups can then be reacted with modalities on other layers, on a silicon surface, on a glass surface, on polymer surfaces, combinations thereof, or the like, thereby forming an adhesive bond. In some embodiments, such adhesive bonds available on the surface of articles disclosed herein, such as laminate mold articles, can increase adhesion between two articles, layers of an article, combinations thereof, or the like. Increasing the bonding strength between layers of a laminate mold can increase the functionality of the article, for example, by increasing the binding strength between laminate layers.

IV.F. Trifunctional PFPE Precursor

According to some embodiments, a trifunctional PFPE precursor can be used to fabricate articles disclosed herein, such as laminate mold articles. The trifunctional PFPE precursor disclosed herein can increase the functionality of an overall article by increasing the number of functional groups that can be added to the material. Moreover, the trifunctional PFPE precursor can provide for increased cross-linking capabilities of the material. According to such embodiments, articles can be synthesized by the following reaction scheme.

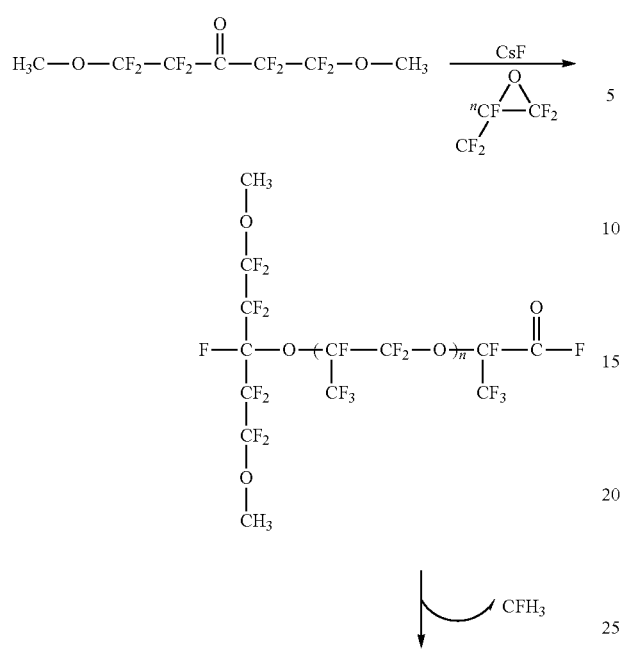
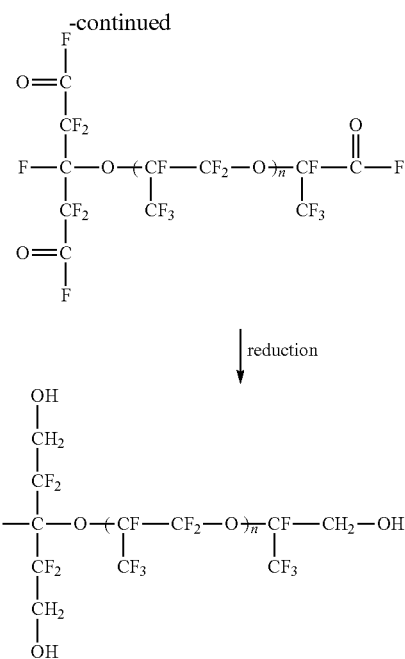
In further embodiments, a trifunctional PFPE precursor for the fabrication of articles, such as for example laminate articles disclosed herein, is synthesized by the following reaction scheme.
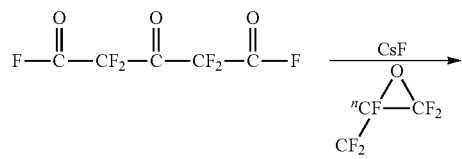
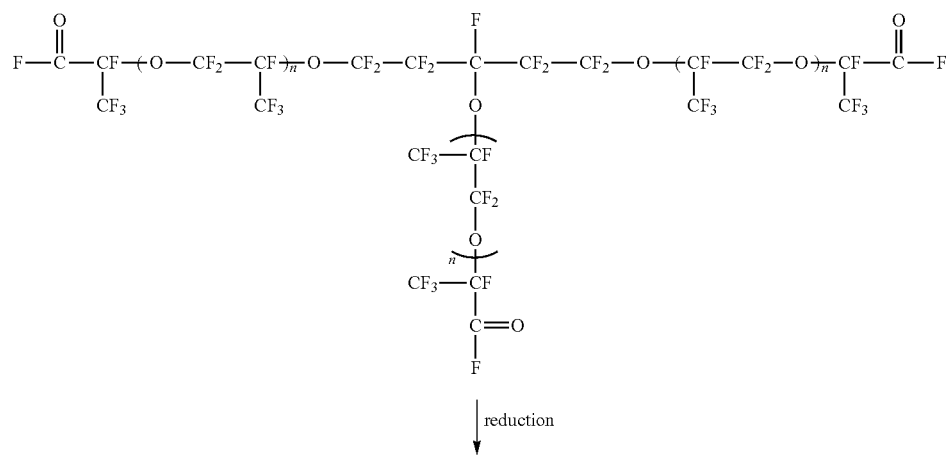

-continued

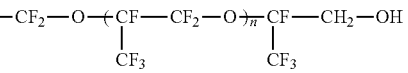
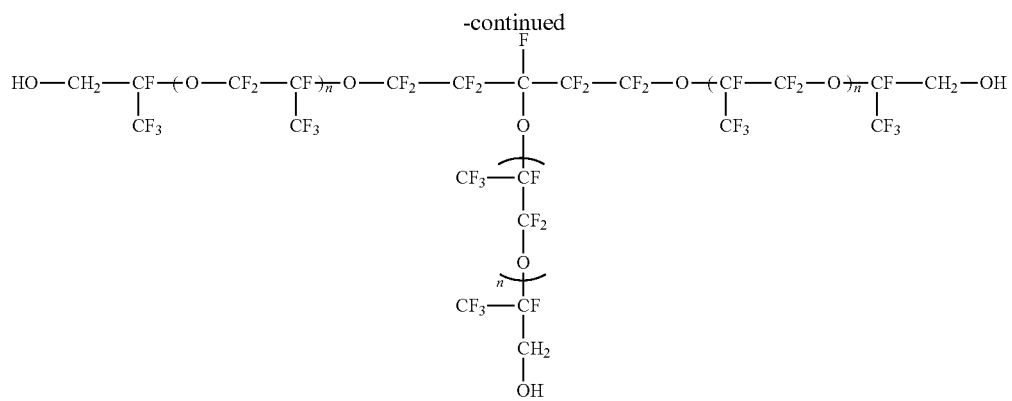

IV.G. Fluoroalkyliodide Precursors for Generating Fluoropolymers and/or PFPE's In some embodiments, functional PFPEs or other fluoropolymers can be generated using fluoroalkyliodide precursors. According to such embodiments, such materials can be modified by insertion of ethylene and then transformed into a host of common functionalities including but not limited to: silanes, Gringard reagents, alcohols, cyano, thiol, epoxides, amines, and carboxylic acids.

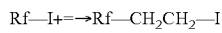

IV.H. Diepoxy Materials

According to some embodiments, one or more of the PFPE precursors useful for fabricating articles disclose herein, such as laminate articles for example, contains diepoxy materials. The diepoxy materials can be synthesized by reaction of PFPE diols with epichlorohydrin according to the reaction scheme below.

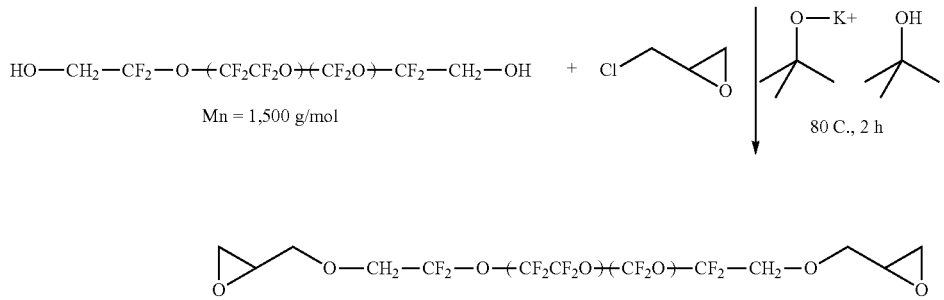

IV.I. Encapped PFPE Chains with Cycloaliphatic Epoxides

In some embodiments, PFPE chains can be encapped with cycloaliphatic epoxides moieties such as cyclohexane epoxides, cyclopentane epoxides, combinations thereof, or the like. In some embodiments, the PFPE diepoxy is a chain-extending material having the structure below synthesized by varying the ratio of diol to epichlorohydrin during the synthesis. Examples of some synthesis procedures are described by Tonelli et al. in *Journal of Polymer Science: Part A: Polymer Chemistry* 1996, Vol 34, 3263, which is incorporated herein by reference in its entirety. Utilizing this method, the mechanical properties of the cured material can be tuned to predetermined standards.

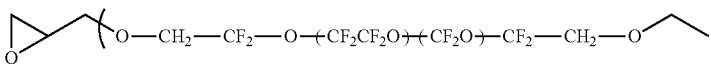

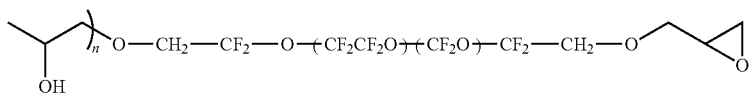

In further embodiments, the secondary alcohol formed in this reaction can be used to attach further functional groups. An example of this is shown below whereby the secondary alcohol is reacted with 2-isocyanatoethyl methacrylate to yield a material with species reactive towards both free radical and cationic curing. Functional groups such as in this example can be utilized to bond surfaces together, such as for example, layers of PFPE material in laminate molds.

-continued

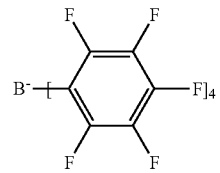

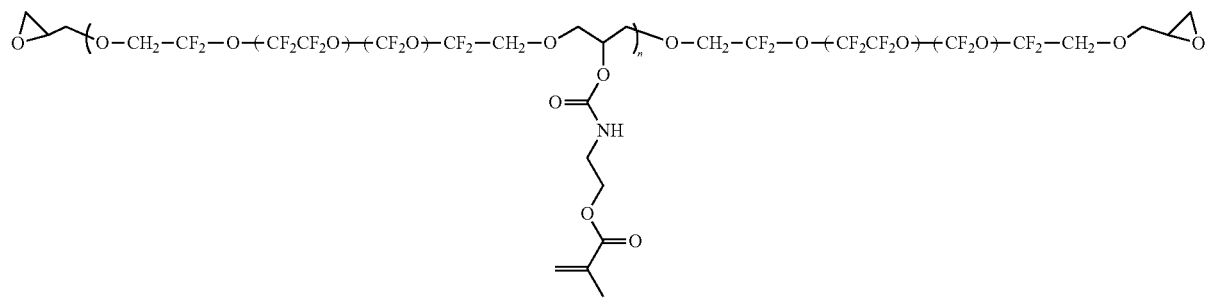

IV.J. PFPE Diepoxy Cured with Diamines

In some embodiments, PFPE diepoxy can be cured with traditional diamines, including but not limited to, 1,6 hexanediamine; isophorone diamine; 1,2 ethanediamine; combinations thereof; and the like. According to some embodiments the diepoxy can be cured with imidazole compounds including those with the following or related structures where R1, R2, and R3 can be a hydrogen atom or other alkyl substituents such as methyl, ethyl, propyl, butyl, fluoroalkyl compounds, combinations thereof, and the like. According to some embodiments, the imidazole agent is added to the PFPE diepoxy in concentrations on the order of between about 1-25 mol % in relation to the epoxy content. In some embodiments the PFPE diepoxy containing an imidazole catalyst is the thermal part of a two cure system, such as described elsewhere herein.

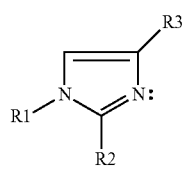

IV.K. PFPE Cured with Photoacid Generators

In some embodiments, a PFPE diepoxy can be cured through the use of photoacid generators (PAGs). The PAGs are dissolved in the PFPE material in concentrations ranging from between about 1 to about 5 mol % relative to epoxy groups and cured by exposure to UV light. Specifically, for example, these photoacid generators can posses the following structure (Rhodorsil™) 2074 (Rhodia, Inc):

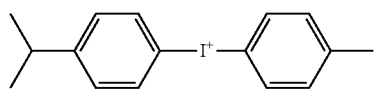

In other embodiments, the photoacid generator can be, for example, Cyracure™ (Dow Corning) possessing the following structure:

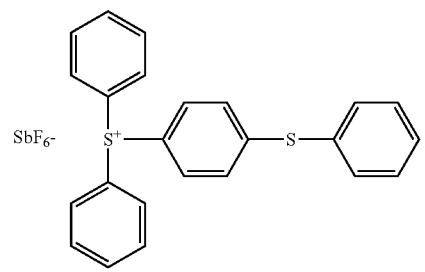

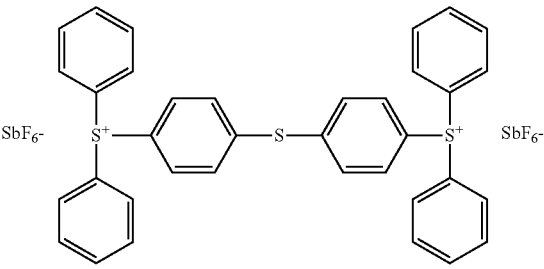

IV.L. PFPE Diol Containing a Poly(Ethylene Glycol)

In some embodiments, commercially available PFPE diols containing a number of poly(ethylene glycol) units can be used as the material for fabrication of a article, such as laminate articles. In other embodiments, the commercially available PFPE diol containing a given number f poly(ethylene glycol) units is used in combination with other materials disclosed herein. Such materials can be useful for dissolving the above described photoinitiators into the PFPE diepoxy and can also be helpful in tuning mechanical properties of the material as the PFPE diol containing a poly(ethylene glycol) unit can react with propagating epoxy units and can be incorporated into the final network.

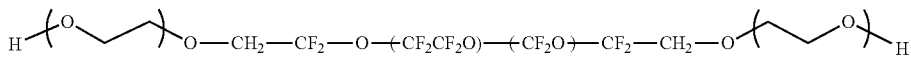

IV.M. PFPE Diols and/or Polyols Mixed with a PFPE Diepoxy

In further embodiments, commercially available PFPE diols and/or polyols can be mixed with a PFPE diepoxy compound to tune mechanical properties by incorporating into the propagating epoxy network during curing.

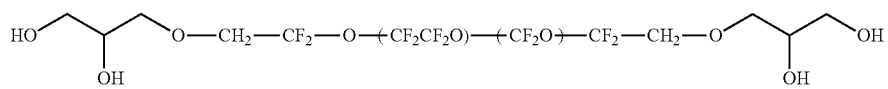

IV.N. PFPE Epoxy-Containing a PAG Blended with a Photoinitiator

In some embodiments, a PFPE epoxy-containing a PAG can be blended with between about 1 and about 5 mole % of a free radical photoinitiator such as, for example, 2,2-dimethoxyacetophenone, 1-hydroxy cyclohexyl phenyl ketone, diethoxyacetophenone, combinations thereof, or the like. These materials, when blended with a PAG, form reactive cationic species which are the product of oxidation by the PAG when the free-radical initiators are activated with UV light, as partially described by Crivello et al. *Macromolecules* 2005, 38, 3584, which is incorporated herein by reference in its entirety. Such cationic species can be capable of initiating epoxy polymerization and/or curing. The use of this method allows the PFPE diepoxy to be cured at a variety of different wavelengths.

IV.O. PFPE Diepoxy Containing a Photoacid Generator and Blended with a PFPE Dimethacrylate In some embodiments, a PFPE diepoxy material containing a photoacid generator can be blended with a PFPE dimethacrylate material containing a free radical photoinitiator and possessing the following structure:

The blended material includes a dual cure material which can be cured at one wavelength, for example, curing the dimethacrylate at 365 nm, and then bonded to other layers of material through activating the curing of the second diepoxy material at another wavelength, such as for example 254 nm.

In this manner, multiple layers of patterned PFPE materials can be bonded and adhered to other substrates such as glass, silicon, other polymeric materials, combinations thereof, and the like at different stages of fabrication of an overall article.

IV.P. Other Materials

According to alternative embodiments, the following materials can be utilized alone, in connection with other materials disclosed herein, or modified by other materials disclosed here and applied to the methods disclosed herein to fabricate the articles disclosed herein. Moreover, end-groups disclosed herein and disclosed in U.S. Pat. Nos. 3,810,874; and 4,818,801, each of which is incorporated herein by reference including all references cited therein.

IV.P.i Diurethane Methacrylate

In some embodiments, the material is or includes diurethane methacrylate having a modulus of about 4.0 MPa and is UV curable with the following structure:

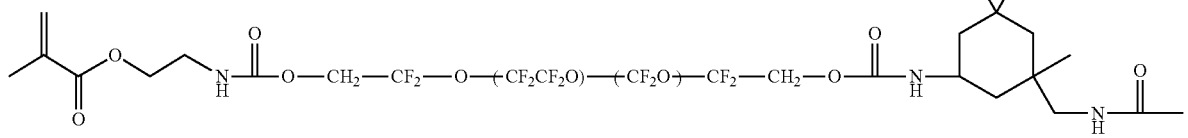

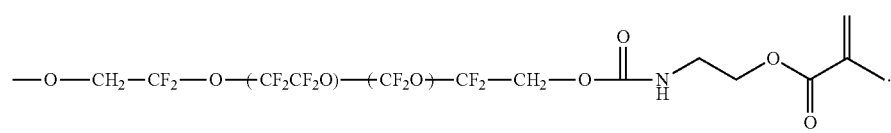

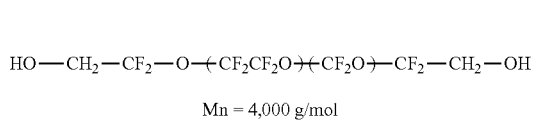 + 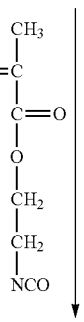
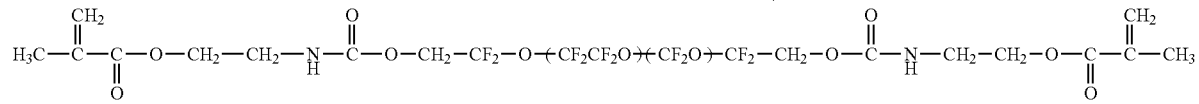
IV.P.ii Chain-Extended Diurethane Methacrylate
In some embodiments, the material is or includes a chain extended diurethane methacrylate, wherein chain extension before end-capping increases molecular weight between crosslinks, a modulus of approximately 2.0 MPa, and is UV curable, having the following structure:

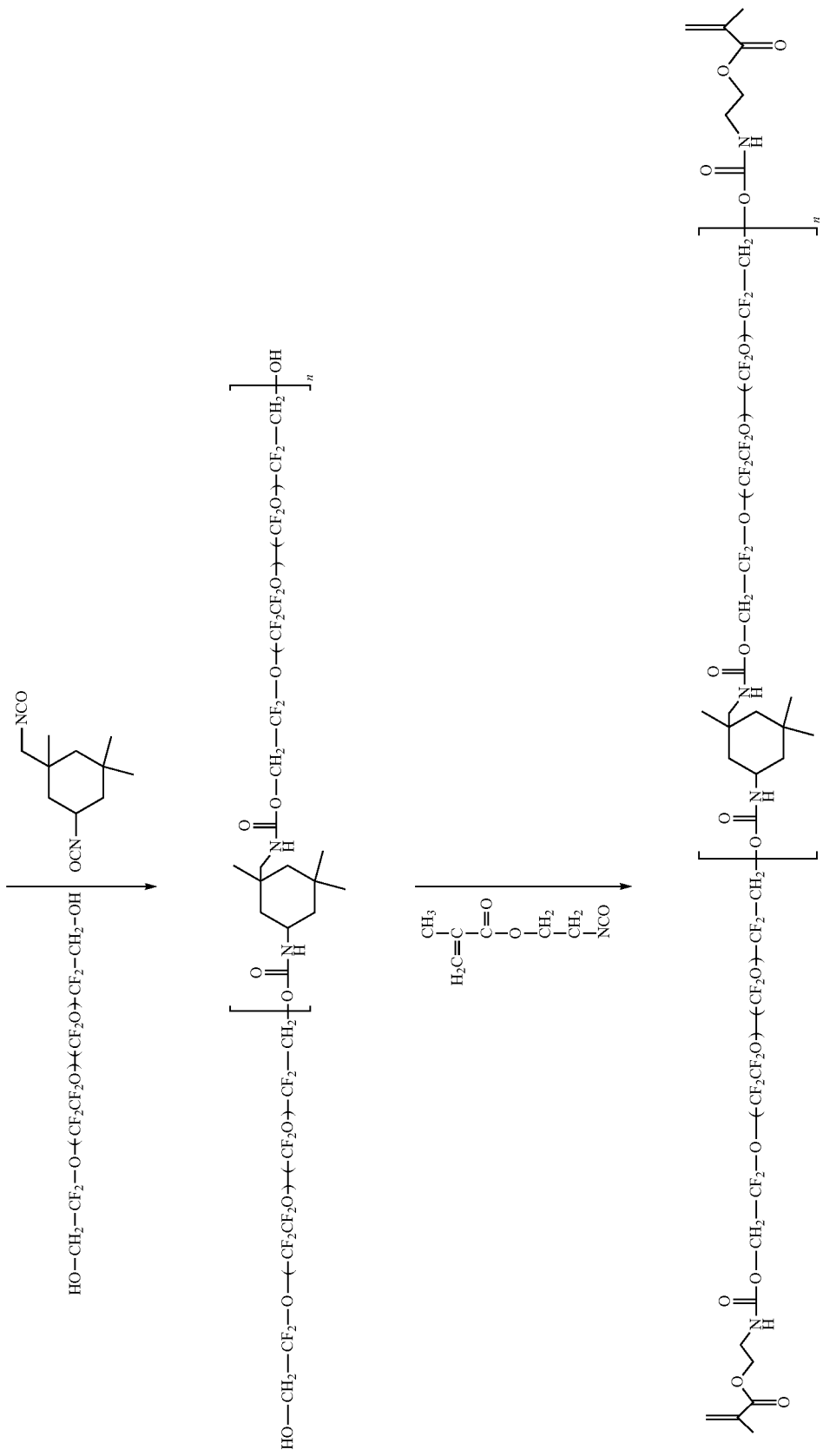

IV.P.iii Diisocyanate

In some embodiments, the material is typically one component of a two-component thermally curable system; may be cured by itself through a moisture cure technique; and has the following structure:

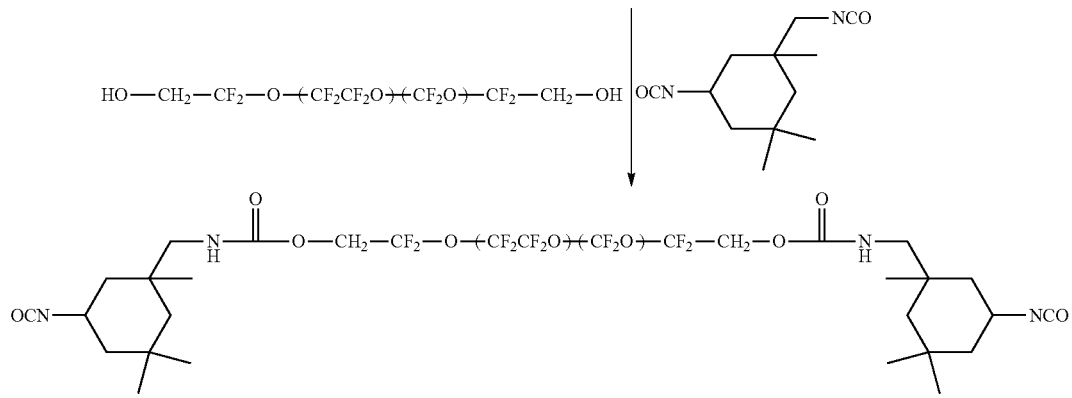

IV.P.iv Chain Extended Diisocyanate

In some embodiments, the material is or includes, one component of a two component thermally curable system; chain extended by linking several PFPE chains together; may be cured by itself through a moisture cure; and includes the following structure:

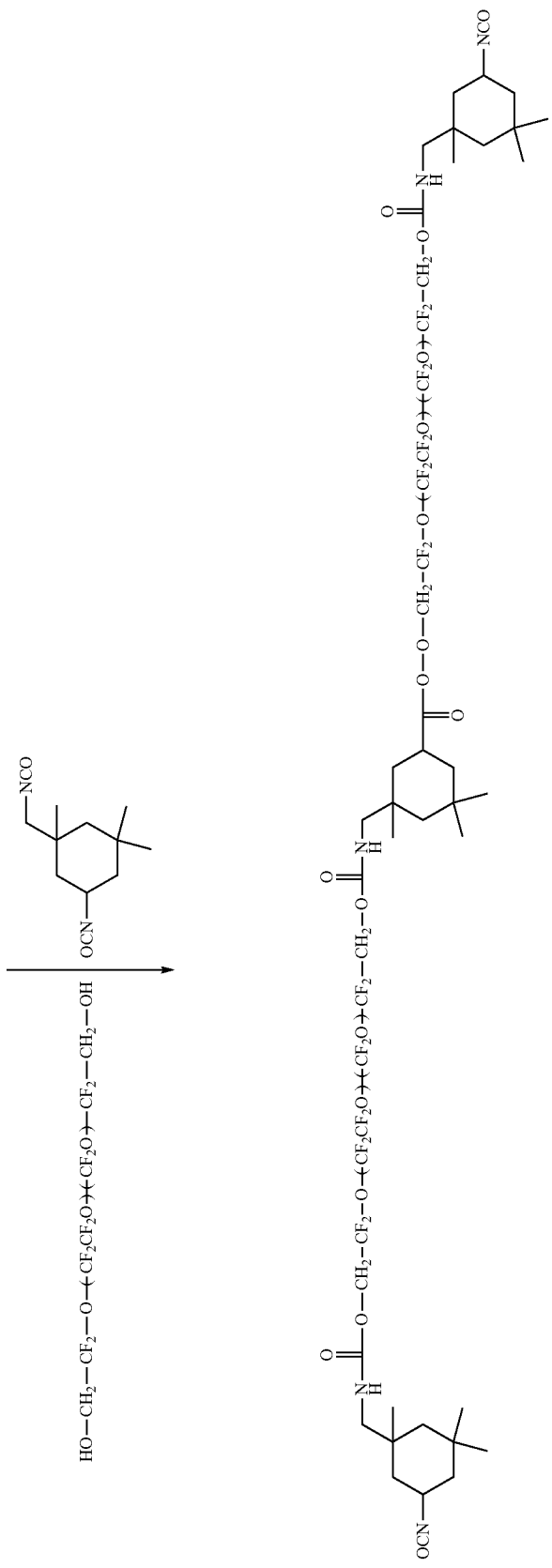

IV.P.v Blocked Diisocyanate

In some embodiments, the material is or includes: one component of a two component thermally curable system; and includes the following structure:

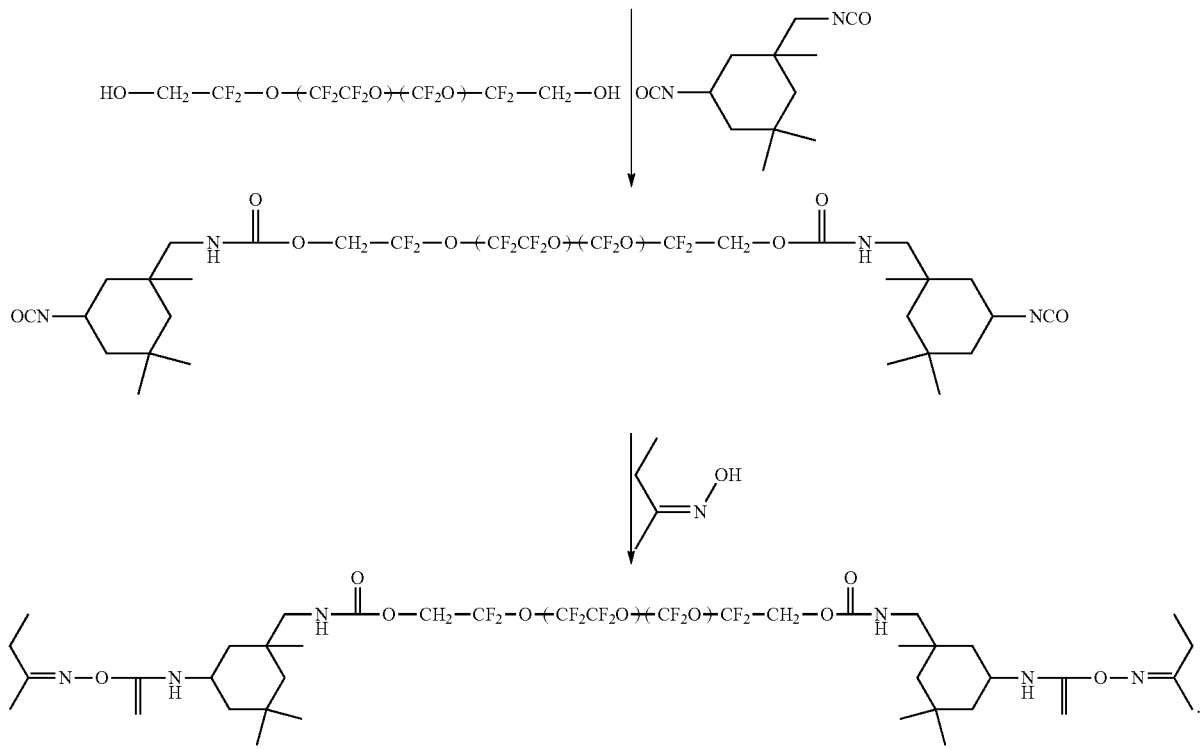

IV.P.vi PFPE Three-Armed Trial

In some embodiments, the material is or includes a PFPE triol as one component of a two-component thermally curable urethane system; includes the benefits of being highly miscible with other PFPE compositions; and includes the following structure:

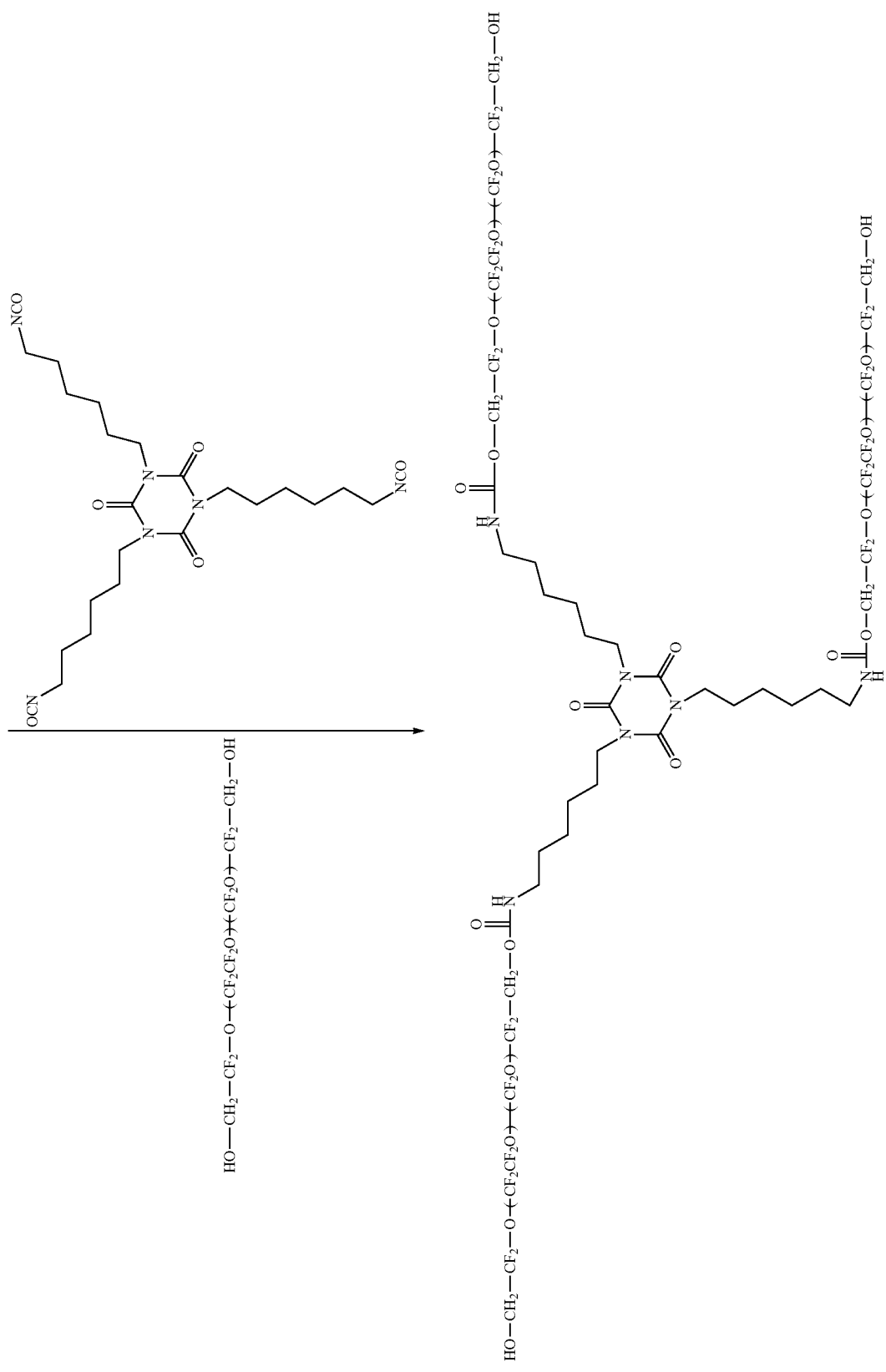

IV.P.vii PFPE DiStyrene

In some embodiments, the material is or includes PFPE distyrene material that is UV curable, highly chemically stable, is useful in making laminate coatings with other compositions, and includes the following structure:

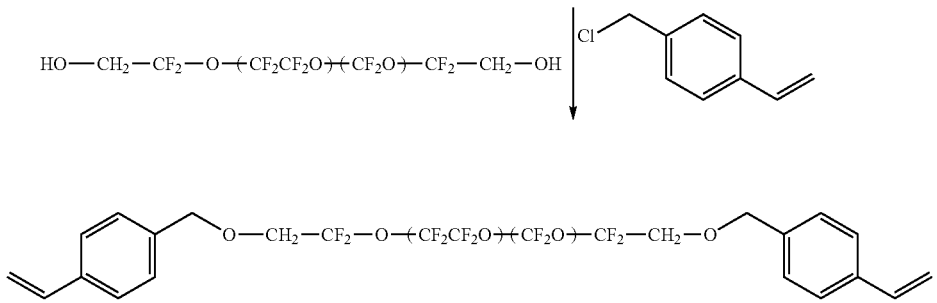

IV.P.viii Diepoxy

In some embodiments, the material can be UV cured; can be thermally cured by itself using imidazoles; can also be thermally cured in a two-component diamine system; is highly Chemically stable; and includes the following structure:

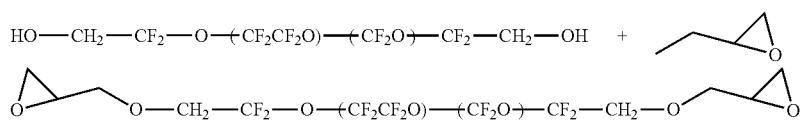

IV.P.ix Diamine

In some embodiments, the material can be thermally cured in a two-component diamine system; has functionality of 6 (3 amines available on each end); is highly chemically stable; and includes the following structure:

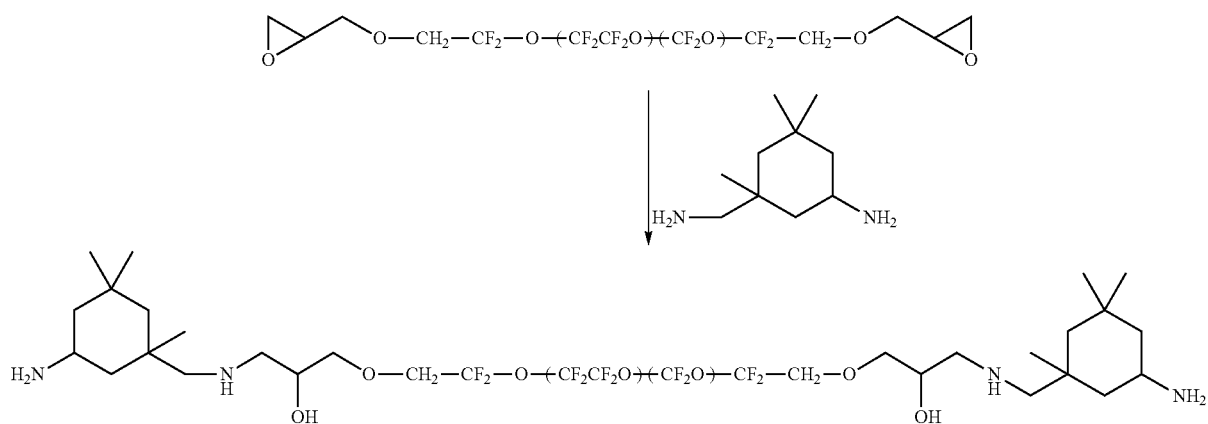

IV.P.x Thermally Cured PU—Tetrol

In some embodiments, the material can be thermally cured in a two-component system, such as for example mixed in a 2:1 molar ratio at about 100-about 130 degrees C.; forms tough, mechanically stable network; the cured network is slightly cloudy due to immiscibility of tetrol; and includes the following structure:

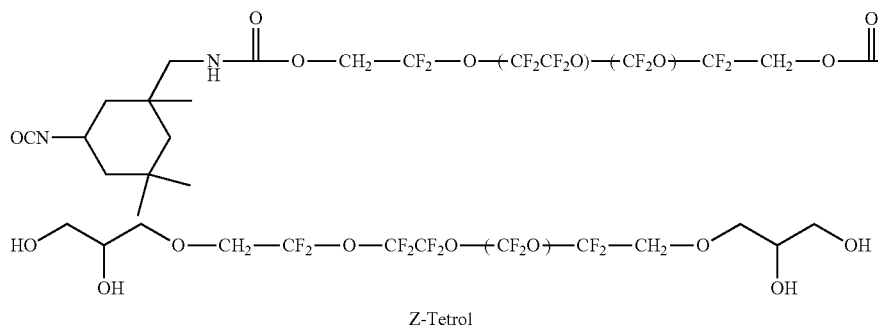
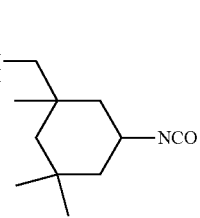
Z-Tetrol
IV.P.xi Thermally Cured PU—Triol
In some embodiments, the material can be thermally cured in a two-component system, such as for example mixed in a 3:2 molar ratio, at about 100-about 130 degrees C.; forms tough, mechanically stable network; Where the cured network is clear and colorless; and includes the following structure:

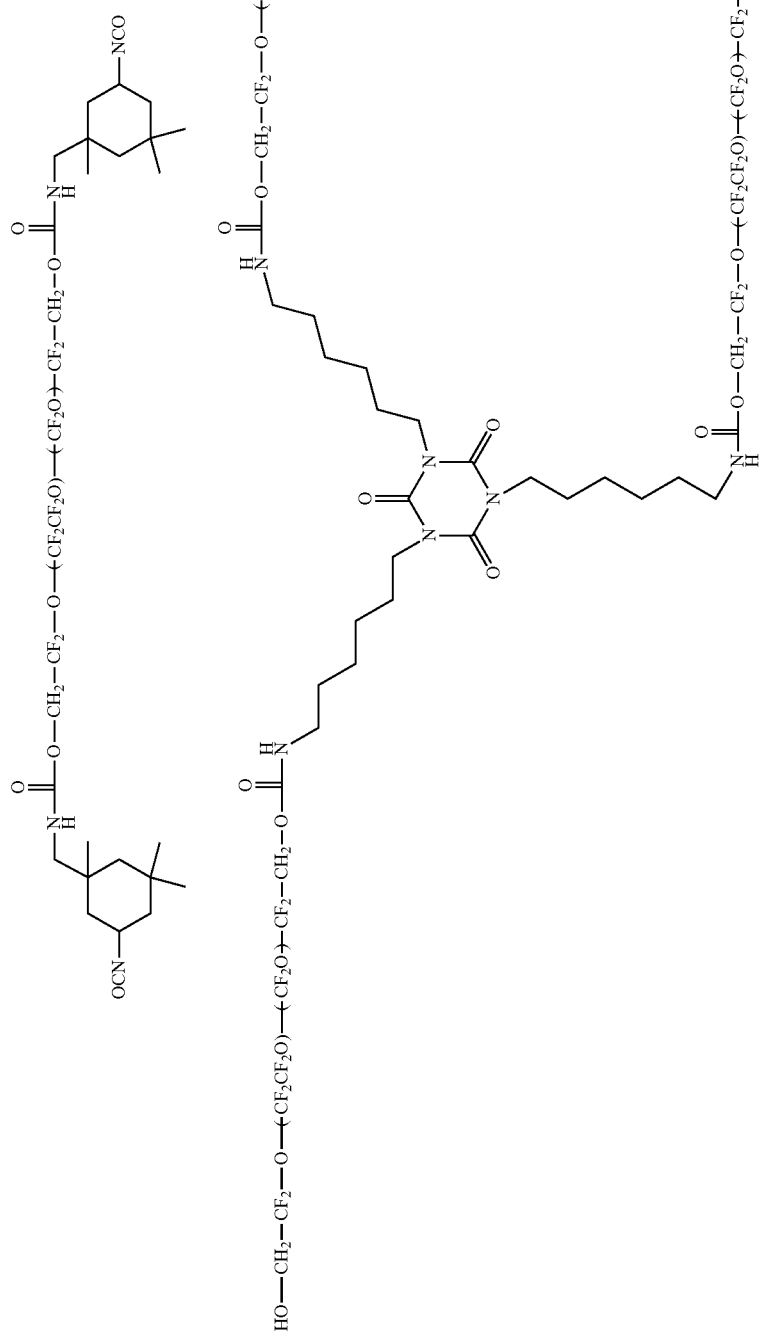

IV.P.xii Thermally Cured Epoxy

In some embodiments, the material can be thermally cured in a two-component system, such as for example mixed in a 3:1 molar ratio, at about 100-about 130 degrees C.; forms mechanically stable network; where the cured network is clear and colorless; has high chemical stability; and includes the following structure:

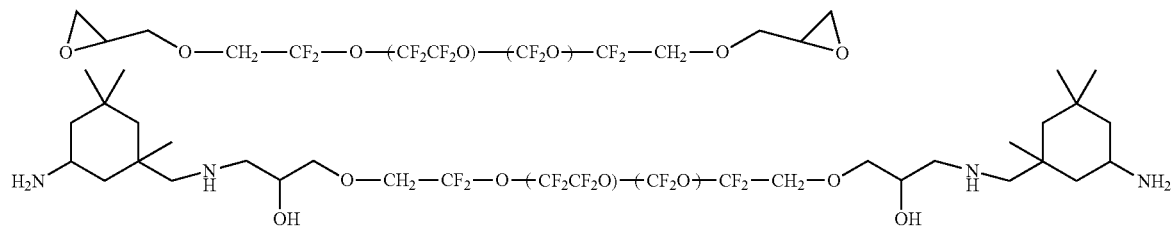

IV. P.xiii UV-Cured Epoxy

In some embodiments, the material is a UV curable composition; includes ZDOL TX used to solubilize PAG; where the cured network is clear and yellow; has high chemical stability; and includes the following structure:

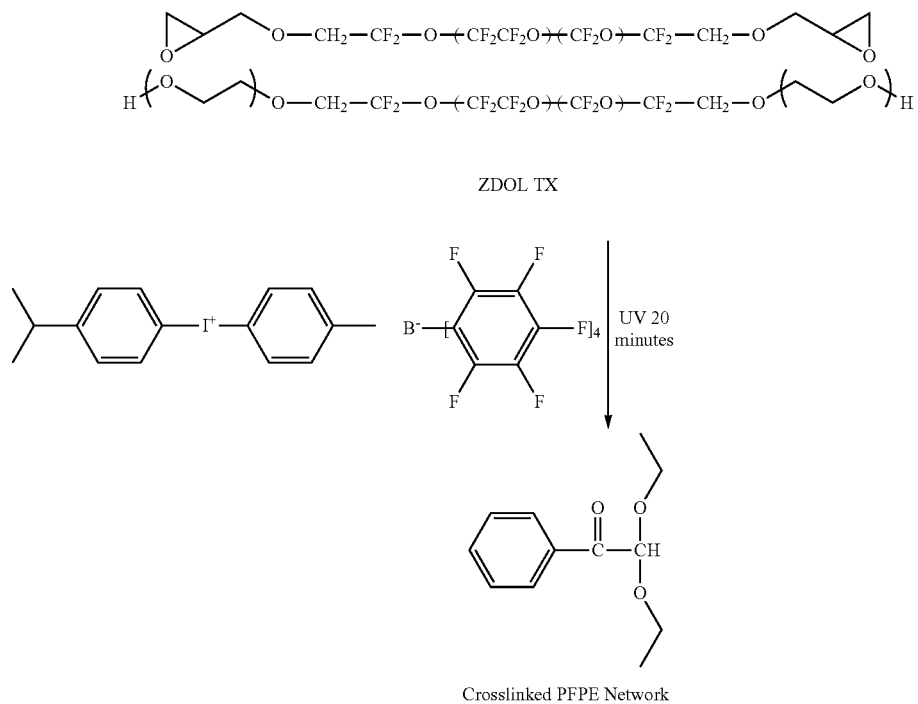

ZDOL TX

Crosslinked PFPE Network

IV.P.ivx UV—Thermal Dual Cure

In some embodiments, the material can be mixed in a 2:1 ratio (UV to thermal); forms cloudy network (tetrol); has a high viscosity; forms a very strong adhesion; has very good mechanical properties; and includes the following structure:

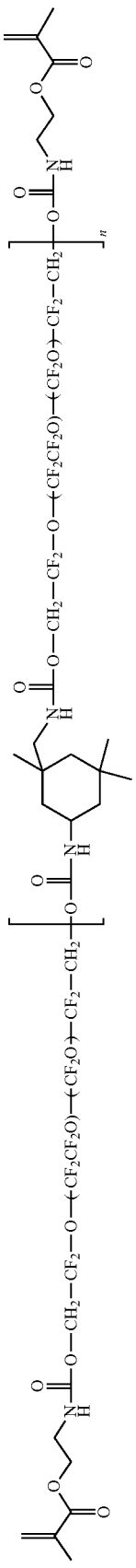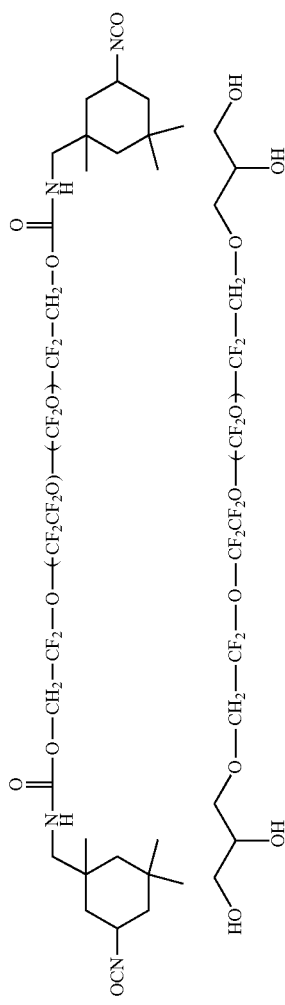

IV.P.xv Orthogonal Cure with Triol

In some embodiments, the material can be mixed in a 2:1 ratio (UV to thermal); forms clear and colorless network; has a high viscosity; forms very strong adhesion; includes very good mechanical properties; and includes the following structure:

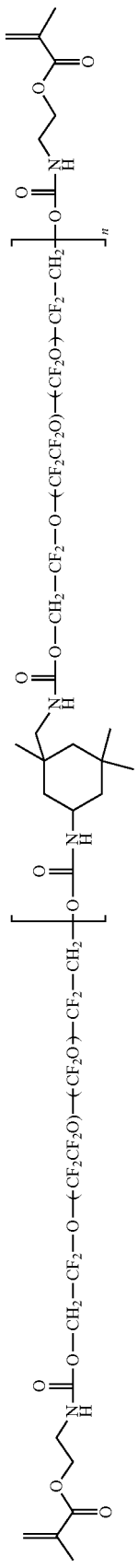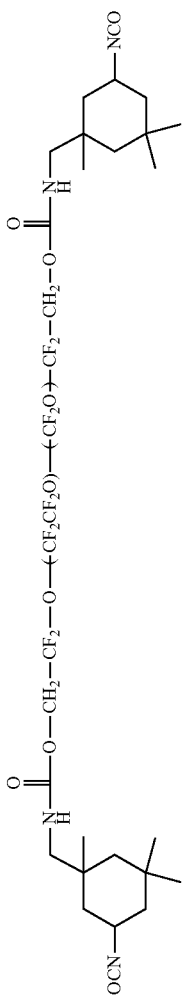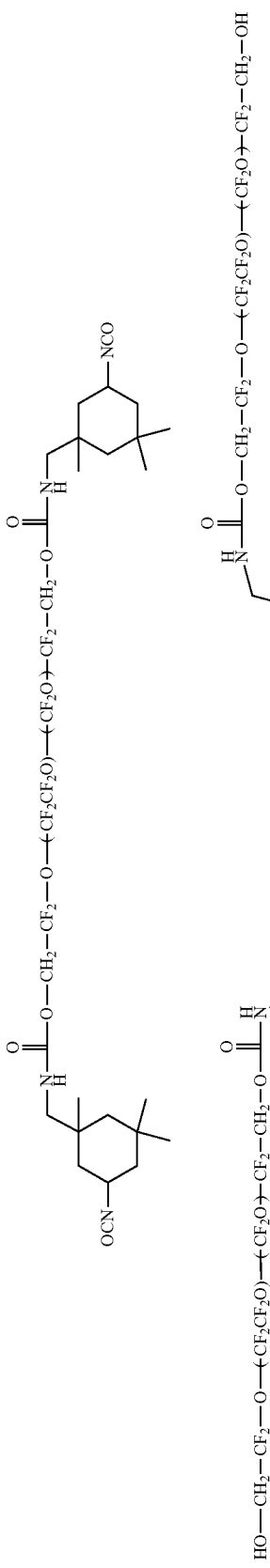

IV.P.xvi UV Orthogonol System

In some embodiments, the material includes ZDOL-TX, which can be mixed in a 1:1 ratio (epoxy to methacrylate); forms clear and yellow network; has strong adhesion properties; has good mechanical properties; and includes the following structure:

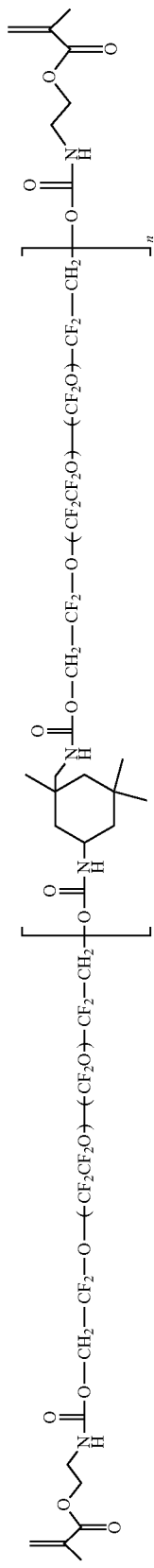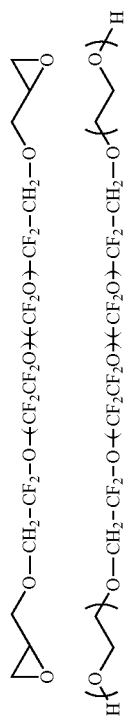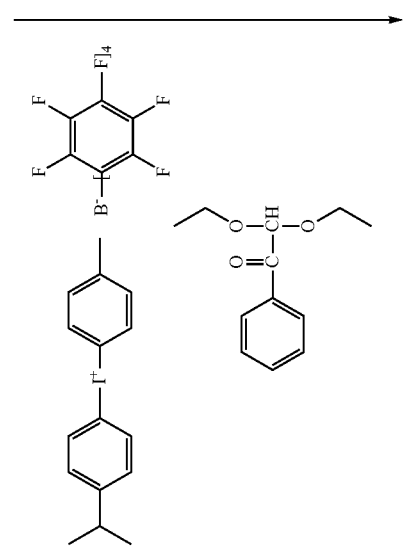

IV.P.xvii UV with Epoxy Dual Cure

In some embodiments, the material forms slightly yellow network; includes a ratio (2:1 UV to thermal); has good mechanical properties; good adhesion; is highly chemical stability; and includes the following structure:

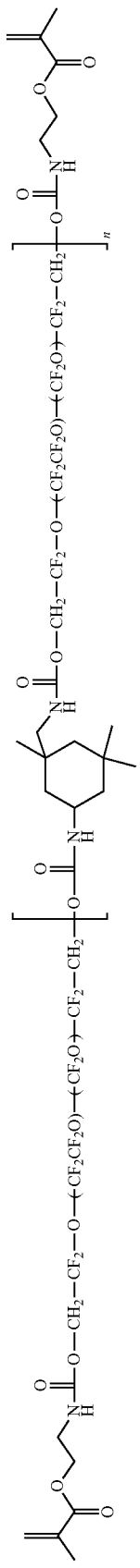
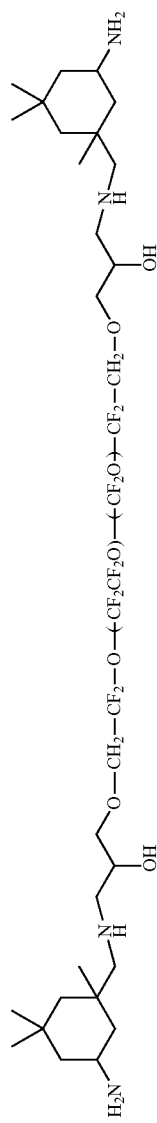

IV.P.xviii Orthogonal with Diisocyanate

In some embodiments, the material is one component thermal component (Isocyanate reacts with urethane linkage on urethane dimethacrylate); has good mechanical properties; forms a strong adhesion; cures to clear, slightly yellow network; and includes the following structure:

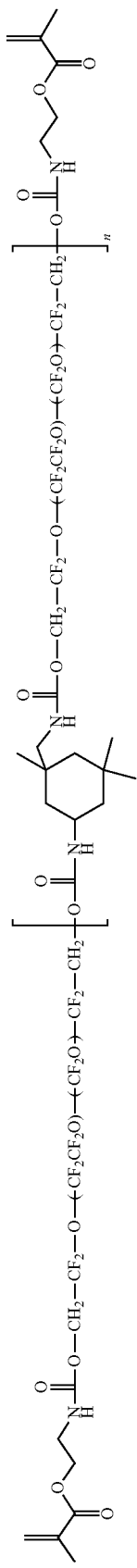
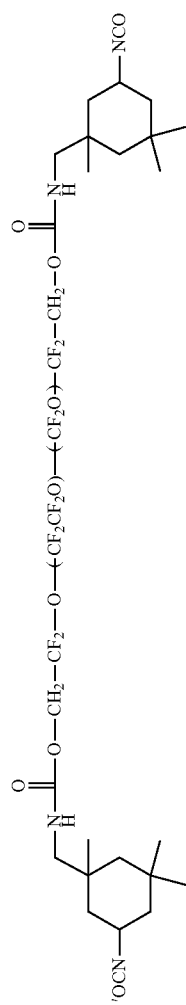

The patents, patent applications and other publications referenced above are hereby incorporated by reference.

V. Examples

Example 1

PFPE Replicate of Cow Subclavian Artery

The aorta and branches were surgically removed from a cow's heart obtained from a butcher and stored under refrigeration. A 1-2" length section having 1" diameter of a subclavian artery was cut on cross-section and cleaned with DI water (See FIG. 3A). The casting resin, polydimethylsiloxane (PDMS) was prepared by weighing out 182 g of the elastomer base, adding 18 g of the curing component, and mixing in a Thinky brand mixer for 2 minutes in the mixing stage and 1 minute in the defoaming stage. The uncured PDMS was poured into a plastic container where the artery section was suspended, completely covering the artery. The PDMS was degassed in a vacuum oven for 30 minutes, then cured at 75° C. for 30 minutes. The plastic container was removed from the oven, allowed to cool, and the plastic removed from the cured PDMS. The casting resin was sliced such that the end of the artery was exposed, and the artery was removed with tweezers leaving a PDMS mold of the artery. The mold was rinsed and dried (see FIG. 3B). A PFPE replicate is generated by pouring PFPE-dimethacrylate (PFPE-DMA) containing 2,2-diethoxyacetophenone into the cavity of the PDMS. The PDMS block is placed in a curing chamber where it is purged with nitrogen for 8 minutes, then cured under 365 nm UV light for 4 minutes. The PDMS is peeled away from the PFPE, leaving a cast replicate of the original artery (see FIG. 3C). The artery and replicate are examined with optical microscopy to confirm precise replication.

Example 2

Molding the Interior of Coronary Arteries 1 inch long sections of coronary arteries with surrounding tissue are dissected from a cows heart. The end of the artery is sealed, and PFPE-dimethacrylate (PFPE-DMA) containing 2,2-diethoxyacetophenone is injected into the open end of the artery. The two artery sections are placed in a curing chamber and cured for 4 minutes under 365 nm light with a light nitrogen purge. The sections are removed from the chamber, photographed (see FIG. 4), and the PFPE plugs are gently removed from the interior of the arteries, revealing a tube-like PFPE structure with a surface identical to that of the artery. Fidelity of the surface replication is confirmed with microscopy.

Example 3

Replication of the Interior of a Pulmonary Vein

A 1.5"×1.5" section of a pulmonary vein was cut from a cows heart, rinsed with DI water, and dried with compressed air. PFPE-dimethacrylate (PFPE-DMA) containing 2,2-diethoxyacetophenone is coated onto the interior vein surface and placed in a curing chamber. The section is cured for 4 minutes under 365 nm light with a light nitrogen purge. The vein is removed from the UV oven, and the cured PFPE is carefully peeled from the surface. Optical microscopy confirms replication of surface features.

Example 4

PFPE Replicate of Heart Muscle Surface

A 1.5"×1.5" section of a chamber of the heart was cut from a cows heart, rinsed with DI water, and dried with compressed air. PFPE-dimethacrylate (PFPE-DMA) containing 2,2-diethoxyacetophenone is coated onto the chamber wall surface and placed in a curing chamber. The section is cured for 4 minutes under 365 nm light with a light nitrogen purge. The muscle is removed from the UV oven, and the cured PFPE is carefully peeled from the surface. Optical microscopy confirms replication of surface features (see FIG. 5).

Example 5

Replication of Blood Vessels in the Liver

A pigs liver is sectioned into 1 inch slices containing cross sections of blood vessels raging in diameter from 0.5 to 2 cm. The sections are rinsed with DI water, and dried with compressed air. One end of the vessels are sealed, and PFPE-dimethacrylate (PFPE-DMA) containing 2,2-diethoxyacetophenone is injected into the vessels. The sections are placed in a curing chamber and cured for 4 minutes under 365 nm light with a light nitrogen purge. The sections are removed from the UV oven and photographed (see FIG. 6). The cured PFPE is carefully separated from the interior of the vessels and pulled out with tweezers. Optical microscopy confirms replication of surface features.

Example 6

Synthetic Replication of Adenovirus Particles Using PRINT Technology

A template, or "master," for perfluoropolyether-dimethacrylate (PFPE-DMA) mold fabrication is generated by dispersing adenovirus particles on a silicon wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro (1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic virus replicates are observed after separation of the PFPE mold and the treated silicon wafer using scanning electron microscopy (SEM) or transmission electron microscopy (TEM). See FIG. 7.

Example 7

Synthetic Replication of Earthworm Hemoglobin Protein Using PRINT Technology A template, or "master," for perfluoropolyether-dimethacrylate (PFPE-DMA) mold fabrication is generated by dispersing earthworm hemoglobin protein on a silicon wafer. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H, 1H, 2H, 2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic protein replicates are observed after separation of the PFPE mold and the treated silicon wafer using scanning electron microscopy (SEM) or transmission electron microscopy (TEM).

Example 8

Fabrication of a Perfluoropolyether-Dimethacrylate (PFPE-DMA) Mold and Replicate from a Template Generated from Block-Copolymer Micelles A template, or "master," for perfluoropolyether-dimethacrylate (PFPE-DMA) mold fabrication is generated by dispersing polystyrene-polyisoprene block copolymer micelles on a freshly-cleaved mica surface. Depending on the block-copolymer composition, self-assembly of PS-b-PI in heptane (a selective solvent for the PI block) results in micelles with well-defined shapes, including spherical, cylindrical, and toroidal micelles, as shown in FIG. 8. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy, and shown in detail in FIG. 8.

Example 9

Fabrication of a Perfluoropolyether-Dimethacrylate (PFPE-DMA) Mold from a Template Generated from Carbon Nanotubes A template, or "master," for perfluoropolyether-dimethacrylate (PFPE-DMA) mold fabrication is generated by dispersing or growing carbon nanotubes on a silicon oxide wafer. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy. Any residual material on the mold was removed by washing with water and isopropanol and/or lightly scrubbing the surface of the mold with an isopropanol-saturated or water-saturated cotton swab. Resultant molds were used to generate replicas by pressing the mold gently against a solution of triacrylate resin/2% DMPA, followed by photopolymerization under a blanket of nitrogen using 365 nm radiation to produce sub-100 nm thick replica films. FIG. 9 shows a carbon nanotube master composed of single-wall (diameter ~1 nm) and multi-wall (diameter-2-5 nm) nanotubes and replicas produced from 1 and 4 kDa PFPE precursors. The replication fidelity is superior for the 1 kDa PFPE precursor than for the 4 kDa precursor due to the lower molecular weight between crosslinks (mesh size). This finding is similar to line edge roughness issues encountered as a function of molecular weight in photolithography. All AFM images of the replicas were obtained on a DI Nanoscope III/Multimode AFM operating in tapping mode. Multiple independent structures were imaged and measured using Nanoscope software to obtain statistics on the sizes of objects on the master and replica film (micelles: n=30; adenovirus particles: n=15; carbon nanotubes: n=10)

We claim:
1. A mold for fabricating nano-structures for medical applications, the mold comprising:
a first surface defining nano-structures configured for fabricating medical articles for treating biologic tissues or conditions,
wherein the nano-structures are less than 500 nm in a dimension, and
wherein the mold comprises an oligomer produced from polymerization of monomers selected from the group consisting of trifluorochloroethylene, trifluoroethylene, hexafluoro-iso-propyl (meth)acrylate, 1H,1H,3H-hexafluorobutyl(meth)acrylate, 1H,1H,5H-octafluoropentyl (meth)acrylate, pentafluorophenyl (meth)acrylate, perfluoro(methyl vinyl ether), 1,1-dihydroperfluorobutyl (meth)acrylate, and combinations thereof, and a functional monomer included in the polymerization of the oligomer, wherein the functional monomer is selected from the group consisting of hydroxyethyl(meth)acrylate, (meth)acrylic acid, vinyl acetate, vinyl sulfonic acid, styrene sulfonic acid, 4-hydroxy styrene, 2-acrylamido-2-methyl propane sulfonate, maleic anhydride, glycidyl methacrylate, isocyanatoethyl methacrylate, and combinations thereof.

2. The mold of claim 1, further comprising a surfactant for adjusting wetting characteristics of the mold.

3. The mold of claim 2, wherein the surfactant is selected from the group consisting of acetylenic alcohol, acetylenic diol, polypropylene oxide), poly(butylene oxide), silicone-poly(ethylene oxide) surfactant, and combinations thereof.

4. The mold of claim 2, wherein the surfactant is selected from the group consisting of a fluorinated hydrocarbon with sulfonic acid end or pendant groups, a fluorinated hydrocarbon with carboxylic acid end or pendant groups, and combinations thereof.

5. The mold of claim 2, wherein the surfactant is selected from the group consisting of perfluorooctanoic acid, perfluorooctane sulfonic acid, and combinations thereof.

6. The mold of claim 1, wherein the medical articles comprise a biocompatible polymer, a protein, a biological molecule, or combinations thereof.

7. The mold of claim 1, wherein the nano-structures defined in the first surface comprise cavities having a broadest dimension of greater than about 1000 nm and a second dimension less than 500 nm.

8. The mold of claim 1, wherein the nano-structures defined in the first surface comprise cavities having a broadest dimension greater than about 2000 nm and a second dimension less than 500 nm.

9. A system for fabricating nano-structures for medical applications, the system comprising:
   a mold having a first surface defining nano-structures for molding articles therefrom,
   wherein the nano-structures are less than 500 nm in a dimension,
   wherein the mold comprises an oligomer produced from polymerization of monomers selected from the group consisting of trifluorochloroethylene, trifluoroethylene, hexafluoro-iso-propyl (meth)acrylate, 1H,1H,3H-hexafluorobutyl(meth)acrylate, 1H,1H,5H-octafluoro-pentyl (meth)acrylate, pentafluorophenyl (meth)acrylate, perfluoro(methyl vinyl ether), 1,1-dihydroperfluorobutyl (meth)acrylate, and combinations thereof, and a functional monomer included in the polymerization of the oligomer, wherein the functional monomer is selected from the group consisting of hydroxyethyl(meth)acrylate, (meth)acrylic acid, vinyl acetate, vinyl sulfonic acid, styrene sulfonic acid, 4-hydroxy styrene, 2-acrylamido-2-methyl propane sulfonate, maleic anhydride, glycidyl methacrylate, isocyanatoethyl methacrylate, and combinations thereof; and
   a biomaterial configured to be molded by the mold and form a medical article that treats or prevents a biologic tissue or condition.

10. The system of claim 9, wherein the mold further comprises a surfactant, wherein the surfactant controls wetting characteristics of the mold.

11. The system of claim 10, wherein the surfactant is selected from the group consisting of acetylenic alcohol, acetylenic diol, polypropylene oxide), poly(butylene oxide), silicone-poly(ethylene oxide) surfactant, a fluorinated hydrocarbon with sulfonic acid end or pendant groups, a fluorinated hydrocarbon with carboxylic acid end or pendant groups, perfluorooctanoic acid, perfluorooctane sulfonic acid, and combinations thereof.

12. The system of claim 9, wherein the medical articles comprise a biocompatible polymer, a protein, a biological molecule, or combinations thereof.

13. The system of claim 9, wherein the nano-structures defined in the first surface of the mold comprise cavities having a broadest dimension of greater than about 1000 nm and a second dimension less than 500 nm.

14. The system of claim 9, wherein the nano-structures defined in the first surface of the mold comprise cavities having a broadest dimension of greater than about 2000 nm and a second dimension less than 500 nm.

* * * * *